US009592280B2

(12) United States Patent
Salamone et al.

(10) Patent No.: US 9,592,280 B2
(45) Date of Patent: Mar. 14, 2017

(54) COMPOSITIONS AND KITS FOR ENZYMATIC DEBRIDEMENT AND METHODS OF USING THE SAME

(71) Applicant: ROCHAL INDUSTRIES, LLP, San Antonio, TX (US)

(72) Inventors: Joseph Charles Salamone, San Antonio, TX (US); Kelly Xiaoyu Chen Leung, San Antonio, TX (US); Ann Beal Salamone, San Antonio, TX (US); Katelyn Elizabeth Reilly, San Antonio, TX (US)

(73) Assignee: ROCHAL INDUSTRIES LLC, San Antonio, TX (US)

( * ) Notice: Subject to any disclaimer, the term of this patent is extended or adjusted under 35 U.S.C. 154(b) by 0 days.

(21) Appl. No.: 14/511,912

(22) Filed: Oct. 10, 2014

(65) Prior Publication Data

US 2016/0101165 A1 Apr. 14, 2016

(51) Int. Cl.

| A61K 38/54 | (2006.01) |
|---|---|
| A61K 31/155 | (2006.01) |
| A61K 31/785 | (2006.01) |
| A61K 38/47 | (2006.01) |
| A61K 45/06 | (2006.01) |
| A61L 26/00 | (2006.01) |
| A61L 15/38 | (2006.01) |
| A61L 15/44 | (2006.01) |

(52) U.S. Cl.
CPC ............ *A61K 38/54* (2013.01); *A61K 31/155* (2013.01); *A61K 31/785* (2013.01); *A61K 38/47* (2013.01); *A61K 45/06* (2013.01); *A61L 15/38* (2013.01); *A61L 15/44* (2013.01); *A61L 26/0047* (2013.01); *A61L 26/0066* (2013.01); *C12Y 302/01001* (2013.01); *C12Y 302/01002* (2013.01); *C12Y 302/01003* (2013.01); *C12Y 304/22032* (2013.01); *C12Y 304/24007* (2013.01); *A61L 2300/206* (2013.01); *A61L 2300/254* (2013.01); *A61L 2300/402* (2013.01); *A61L 2300/404* (2013.01); *A61L 2300/45* (2013.01)

(58) Field of Classification Search
USPC ........................................................ 424/94.2
See application file for complete search history.

(56) References Cited

U.S. PATENT DOCUMENTS

| 2,120,667 | A | | 6/1938 | Gruskin | |
|---|---|---|---|---|---|
| 2,917,433 | A | | 12/1959 | Goldman | |
| 3,003,917 | A | * | 10/1961 | Beiler et al. | 424/94.2 |
| 3,409,719 | A | | 11/1968 | Noe | |
| 3,681,197 | A | * | 8/1972 | Smith | A61K 8/66 |
| | | | | | 424/50 |
| 4,652,524 | A | | 3/1987 | Modrovich et al. | |
| 4,668,228 | A | | 5/1987 | Bolton | |
| 4,717,737 | A | | 1/1988 | Kern | |
| 4,719,235 | A | | 1/1988 | Kern | |
| 4,772,465 | A | | 9/1988 | Collins | |
| 4,885,310 | A | | 12/1989 | Kern | |
| 5,120,656 | A | | 6/1992 | O'Leary | |
| 5,206,026 | A | | 4/1993 | Sharik | |
| 5,543,149 | A | | 8/1996 | Rubin | |
| 5,591,442 | A | | 1/1997 | Diehl et al. | |
| 5,670,142 | A | | 9/1997 | Rubin | |
| 6,548,556 | B2 | | 4/2003 | Hobson | |
| 7,368,128 | B2 | | 5/2008 | Qvist | |
| 8,119,124 | B2 | | 2/2012 | Gorecki | |
| 8,486,664 | B2 | | 7/2013 | Keller | |
| 8,540,983 | B2 | | 9/2013 | Gorecki | |
| 8,754,045 | B2 | | 6/2014 | Livingston | |
| 9,107,419 | B2 | | 8/2015 | Fallon et al. | |
| 2002/0114798 | A1 | | 8/2002 | Hobson | |
| 2004/0076671 | A1 | * | 4/2004 | Tippett | 424/484 |
| 2004/0105874 | A1 | * | 6/2004 | Bott et al. | 424/401 |
| 2007/0237812 | A1 | * | 10/2007 | Patel et al. | 424/446 |
| 2008/0044459 | A1 | | 2/2008 | Livingston | |
| 2013/0202581 | A1 | * | 8/2013 | Fallon | A61K 38/54 |
| | | | | | 424/94.21 |
| 2013/0273026 | A1 | | 10/2013 | Gavini et al. | |
| 2015/0086529 | A1 | | 3/2015 | Hillenbrand | |

FOREIGN PATENT DOCUMENTS

| WO | 84/02846 | | 8/1984 | | |
|---|---|---|---|---|---|
| WO | 99/46368 | | 9/1999 | | |
| WO | 02/08377 | | 1/2002 | | |
| WO | 2007/144856 | | 12/2007 | | |
| WO | 2008/063229 | | 5/2008 | | |
| WO | 2010/004367 | | 1/2010 | | |
| WO | 2012/013646 | | 2/2012 | | |
| WO | 2012/155027 | | 11/2012 | | |
| WO | WO2013016255 | * | 1/2013 | | A61K 9/00 |

OTHER PUBLICATIONS

Souza et al. Application of microbial alpha-amylase in industry—a review. Brazilian Journal of Microbiology. 2010;41:850-861.*

Loo et al. Effects of hydrogen peroxide on wound healing in mice in relation to oxidative damage. PLoS One. 2012;7(11):e49215:1-13.*

* cited by examiner

*Primary Examiner* — Lynn Y Fan
(74) *Attorney, Agent, or Firm* — Duane Morris LLP; J. Rodman Steele, Jr.; Gregory M. Lefkowitz (57) ABSTRACT

A debridement enzyme for necrotic tissue is described that is not dependent upon proteolytic enzymatic activity but instead utilizes the amylase family of enzymes. The amylases ($\alpha$-, $\beta$-, $\gamma$-amylase) are noted for the cleavage of the $\alpha$-glycosidic bonds of polysaccharides, yielding lower molecular weight carbohydrate/sugar fragments. It has now been found that $\alpha$-amylase is effective in the debridement of devitalized tissue.

22 Claims, 3 Drawing Sheets

COMPOSITIONS AND KITS FOR ENZYMATIC DEBRIDEMENT AND METHODS OF USING THE SAME

FIELD OF INVENTION

Enzymatic debridement of necrotic tissue in wounds is often used when surgical debridement is unavailable or undesirable. This invention relates generally to the debridement of devitalized tissue by use of enzymes, specifically enzymes that cleave carbohydrate α-1,4-glycodisic linkages in polysaccharides, such as those of the amylase family, in contrast to the cleavage of peptide bonds in proteins.

BACKGROUND OF THE INVENTION

Wound healing is impaired by the presence of necrotic tissue, which contains dead cells and debris within second (deep partial thickness) and third degree (full thickness) burns (eschar) and chronic ulcers (e.g., diabetic ulcers). Necrotic tissue is devitalized tissue and its accumulation can result in a prolonged inflammatory response and mechanical obstruction of the wound contraction process with impeded reepithelialization, preventing wounds from healing and, if needed, hindering the wound bed from taking skin grafts. Necrotic tissue is susceptible to bacterial infection, which further impedes wound healing, and may induce sepsis in severe cases. When necrotic tissue is yellow or tan colored and a stringy mass in appearance, it is often termed slough, and when the tissue is desiccated and forms a thick and leathery texture, it is referred to as eschar. Debridement (removal) of devitalized tissue is needed to enhance wound closure. The debriding composition of this invention is thus useful in treating wounds.

Removing necrotic tissue helps to restore circulation at the wound site as adequate oxygen delivery to the wound is critical to healing. Methods to debride necrotic tissue include surgical debridement, enzymatic debridement, autolytic debridement, biological debridement, and mechanical debridement, with surgical and enzymatic debridement being most prevalent. Surgical debridement is the fastest and most efficient method for debridement and is performed by trained medical personnel/surgeons. However, viable tissue can be inadvertently removed because of a lack of clear demarcation between necrotic and viable tissue, resulting in an enlarged wound area and increased blood loss. Enzymatic debridement utilizes less training and it is generally performed by nursing/clinical staff, often requiring a longer duration of treatment for necrotic tissue removal. Enzymatic debridement involves the use of enzymes obtained from outside the body to remove non-living tissue. Debridement enzymes cleave (cut, digest, hydrolyze) large components of biological materials, particularly biomacromolecules into smaller molecules that can dissolve and be removed. Most debridement enzymes function as proteases by cleaving protein polymer chains, and a wide variety of proteases have been studied in this regard. Debridement enzymes are fast acting catalysts that produce slough of necrotic tissue. Fibrinolysin is a plasma enzyme which, after being activated, attacks fibroin components in blood clots and exudates. Deoxyribonuclease is a pancreatic enzyme that specifically attacks nucleoprotein components of purulent exudates. Trypsin and chymotrypsin are nonspecific pancreatic enzymes, but can sever protein backbones at specific amino acid residues. Enzymes from other animals include krillase, a protease derived from Antarctic krill. Tropical fruit-bearing plants provide a major source of debridement enzymes. Bromelain is a group of proteolytic enzymes from the stem of pineapple plants, which include three cysteine proteases. Papain is a nonspecific cysteine protease from papaya latex that cleaves a wide variety of substances in necrotic tissues, including fibroin, collagen, and elastin. Ficin is a nonspecific cysteine protease of similar operating pH characteristics, and is derived from a plant latex of the ficus (fig) plant. Bacteria are also a source of debridement enzymes. Subtilisins, derived from *Bacillus subtilis*, are mixtures of nonspecific, water-soluble serine proteases that degrade necrotic tissues. Collagenases, which are metallopeptidases, are proteolytic enzymes that degrade collagen and are derived from *Clostridium histolyticum*. Vibriolysin is another collagen-attacking metallopeptidase, and it is derived from the bacteria *Vibrio proteolyticus*. Thermolysin is a bacterial debridement enzyme from *Bacillus thermoproteolyticus* that acts nonspecifically with outstanding productivity, even at high temperature. Streptokinase, a fibrinogen activating protease from *Streptococcus* spp. and streptodomase, a deoxyribonuclease from hemolytic streptococci, has also been used in debridement (US Patent Application Number 2008/0044459).

A number of non-FDA regulated topical proteolytic enzyme products were marketed prior to 2009 for enzymatic debridement but manufacturing and distribution were stopped by FDA because of adverse allergic events and/or lack of efficacy, including papain (papaya), trypsin and chymotrypsin (pancreatic enzymes), and *Bacillus subtilis* proteases. Currently, there are two proteolytic enzymatic debridement products available in the United States, FDA approved Santyl® Ointment (Smith & Nephew), a collagenase derived from *Clostridium histolyticum* that selectively digests triple helical collagen and utilizes 250 collagenase Units per gram of white petrolatum, and Debrase® Gel Dressing (NexoBrid), a mixture of bromelain enzymes derived from *Ananas comosus* (pineapple). Importantly, Santyl® Ointment cannot be used in conjunction with silver and iodine antimicrobials as they deactivate the collagenase. Debrase®(MediWound Ltd.) has recently received FDA orphan drug status for eschar debridement.

U.S. Pat. No. 4,668,228 discloses a debriding tape comprising an adhesive mass on a non-gel, non-bioerodable, biocompatible occlusive or semi-occlusive backing, where an effective amount of a debriding proteolytic enzyme in dry powdered form is situated on the adhesive surface. When the powder is brought into contact with wound exudates the entire load of enzymes is released immediately.

In U.S. Pat. No. 5,206,026 is disclosed a film for instantaneous delivery of a proteolytic enzyme to a wound. When exposed to aqueous liquid the film rapidly dissolves, thus releasing its contents of enzymes simultaneously.

In U.S. Patent Application 2002/0114798 is disclosed an enzymatic wound debrider that uses a combination of a proteolytic enzyme and an anhydrous hydrophilic poloxamer carrier.

In U.S. Pat. No. 5,120,656 there is provided a process for the debridement of harvested bone having its periosteum intact, which comprises contacting the periosteum with a solution of enzyme selected from the group consisting of proteolytic collagen-digesting enzyme and mixtures thereof under enzyme activity promoting conditions to loosen the periosteum from the underlying bone surface and removing the loosened periosteum from the bone.

In U.S. Pat. No. 7,368,128, a dressing for debridement of necrotic and non-viable tissue in a wound is described, wherein the dressing comprises an effective amount of one or more proteolytic enzymes incorporated in a degradable polymeric material. The dressing of the invention provides effective debridement of necrotic wounds over a prolonged period of time, as the enzymes may be released over time.

In International Patent Publication Number WO 2012/155027, wound debridement compositions contain the proteolytic enzyme Seaprose (also known as Protease S, from the fungus *Aspergillus melleus*). The major enzyme in Seaprose is a semi-alkaline protease with a molecular weight around 31 kDa. It can also contain other enzymes such as amylase, a hydrolytic enzyme that breaks down carbohydrates.

In International Patent Publication Number WO1984/002846, a topical ointment for skin surface wounds is described comprising wound-healing amounts papain, bromelain, trypsin, chymotrypsin, pancreatin, lipase, amylase, aloe extract and an organic astringent agent formulated in a carrier mixture of penetrating and non-penetrating emollient oils and a polyhydric alcohol emollient, with a plurality of protease. The ointment is reported to reduce inflammation at the site of skin-surface wounds and acts to enhance the normal anti-inflammatory activities of the body.

In U.S. Pat. No. 6,548,556 it is reported that a proteolytic enzyme has in part or in total the capacity to hydrolyze peptide amide bonds and that such enzymes may also have some inherent lipolytic and/or amylolytic activity associated with the proteolytic activity, with the preferred proteolytic enzyme being papain. Other suitable proteolytic enzymes include trypsin, chymotrypsin, streptokinase, streptodormase, ficin, pepsin, carboxypeptidase, aminopeptidase, chymopapain, bromelain, as well as other suitable enzymes, such as pancreatin, trypsin, collagenase, keratinase, carboxylase, aminopeptidase, elastase, and aspergillopeptidase. Pancreatin contains a mixture of peptide hydrolases/proteases (trypsin, chymotrypsin, elastase, carboxypeptidase A, carboxypeptidase B), lipolytic enzymes (lipase, phospholipase A2, phospholipase B, cholinesterase, cholesterol esterase), glycosidases (α-amylase, glucosidase), and nucleases (deoxyribonuclease I, deoxyribonuclease II, ribonuclease).

Mixed debriding agent enzymes from *Bacillus subtilis* are described in U.S. Pat. No. 3,409,719. This enzyme product is reported to exhibit proteolytic activity against casein (phosphoprotein) and similar activity against hemoglobin (metalloprotein). It also exhibits amylolytic activity against gelatinized starch. It is capable of rapid lysis of fibrin, denatured collagen, elastin and exudate, which are reported to be the principal tissue protein components in the wound. The mixed enzyme compositions are shown in Table I of U.S. Pat. No. 3,409,719 to contain a minimum of amylase to proteases, ranging from 6.3% amylase and 93.7% proteases to 18.2% amylase and 81.8% proteases.

Severe burn wounds require surgical debridement in order to quickly apply antimicrobials and dressings to reduce the risk of infection, (e.g., *Pseudomonas aeruginosa* sepsis, U.S. Pat. No. 4,772,465) and to prepare the wound bed for healing or subsequent skin grafting. Because of the potential of enhanced bleeding from viable tissue removal, enzymatic debridement may be preferable for removal of necrotic tissue. Wound healing is also difficult for diabetics due to cardiovascular insufficiency and neuropathy; hence, enlarging the diabetic ulcer size by surgical debridement may not be desirable, and a critical need exists for improved debridement for diabetic ulcers.

In International Patent Publication Number WO1999046368 a method for treating wounds comprising the step of administering an effective amount of a carbohydrate-active enzyme is discussed, which is reported to have broad-specificity for debriding burns and other wounds. Because of the high concentrations of glycosaminoglycans (GAGs) in skin, in burn patients enzymes that degrade glycosaminoglycans are considered to be useful adjuncts to burn wound debridement. Glycosaminoglycans are sugar chains consisting of repeating polymers of acidic polysaccharides, composed of building blocks of the following sugars in various combinations: galactose, glucose, N-acetylglucosamine, N-acetylgalactosamine, glucuronic acid, galacturonic acid and iduronic acid. It is known that carbohydrates have important roles in the functioning of living organisms. In addition to their metabolic roles, carbohydrates are structural components of the human body, being covalently attached to numerous other entities such as proteins (i.e., as glycoproteins). Since human skin is reported to contain 10% by weight of glycosaminoglycans (which include heparin, heparan sulfate, chondroitin sulfate, hyaluronic acid (hyaluronan), dermatan sulfate, and keratan sulfate, with chondroitin sulfate being the most prevalent glycosaminoglycan. Chondroitin sulfate also has β-1,3- and β-1,4-linkages between predominant monomeric units. The term "carbohydrate-active enzyme" as used to specifically encompass carbohydrate reducing enzymes, where examples of such enzymes include glycosaminoglycan reducing enzymes such as hyaluronidases, chondroitinases, dermatanases, heparanases, hepanrnases and keratanases, with preferred carbohydrate-active enzymes of chondroitinases and hyaluronidases.

Infection control is also a significant unaddressed need in debridement. Burn eschar is typically dry necrotic tissue not readily infected, but sepsis can occur with second and third degree burns; therefore, having antimicrobials in the eschar and wound bed during early stages of eschar (necrotic tissue) removal is highly desirable. In contrast to burn eschar, chronic wound (diabetic ulcer) necrotic tissue appears to promote bacterial colonization, supported by the presence of water and nutrient sources from dead cells and debris. Necrotic tissue in wounds may be associated with infection, while a majority of chronic wounds are infected with microorganism biofilm.

A difficulty in the use of proteolytic enzymes for debridement of necrotic tissue is their ability for auto-digestion in aqueous solution, in addition to their potential difficulty with adverse allergic events, hypersensitivity and/or lack of efficacy. It is thus desirable to identify a debridement composition, having a high debridement efficacy for necrotic tissue, that is clinically simple to use, exhibits a suitable shelf-life, and is non-allergenic.

DETAILED DESCRIPTION OF THE INVENTION

In this investigation a novel composition and approach to enzymatic debridement is considered through the presumed cleavage of glycosidic bonds in and/or between glycosaminoglycan polysaccharides and collagen fibrils, and not by cleavage of peptide bonds of collagen by proteases, as has been done with previous enzymatic debridement products. It was unexpectedly found that amylase, an enzyme noted for cleavage of α-1,4-glycosidic bonds, such as in the catalyzed hydrolysis of starch into low molecular weight sugars, is effective in the debridement of devitalized or necrotic tissue. These unique compositions provide high efficiency enzymatic debridement compositions, with a suitable shelf-life, without allergic reactions.

The debriding formulations described herein contain various types of the enzyme amylase. Amylases (α-, β-, γ-amylase) are a family of enzymes that preferentially hydrolyze the α-glycosidic bonds of polysaccharides, yielding lower molecular weight carbohydrate/sugar fragments. In some embodiments, α-amylase is used as the amylase. Amylase occurs naturally in humans and other mammals, and it is also is found in plants, bacteria and fungi.

The physical behavior of skin tissue is determined primarily by an extensive extracellular matrix (ECM). The ECM is composed of an interlocking mesh of fibrous proteins and glycosaminoglycans (GAGs). The GAGs are carbohydrate polymers and are usually attached to ECM proteins, forming proteoglycans. In skin, type I collagen is the main protein component of the ECM and the main proteoglycan components are decorin and versican. Presumably, these core proteins bind to the surface of type I collagen fibrils, which provide mechanical strength to skin. Proteoglycan binding is required for appropriate assembly of collagen fibrils in the ECM and inhibits cleavage of collagen fibrils by matrix metalloproteases. Proteoglycans are composed of a glycoprotein core to which one or several GAG chains are covalently bonded. Four different classes of glycosaminoglycans exist in vertebrates, chondroitin sulfate, dermatan sulfate, keratan sulfate, and heparan sulfate/heparin. Hyaluronan (hyaluronic acid) is one of the chief components of the extracellular matrix, and it contributes significantly to cell proliferation and migration. However, unlike the other glycosaminoglycans, hyaluronan does not attach to proteins to form proteoglycans but binds and retains water molecules and fills the gaps between collagen fibrils.

The GAGs are attached to a serine residue of the core protein by both glycosidic (β-1,4- (primarily by chondroitin sulfate, dermatan sulfate) and α-1,4-bonds (primarily by heparan sulfate/heparin), with the predominant GAG being chondroitin sulfate. For internal linkages, hyaluronan and chondroitin sulfate are predominantly composed of β-1,3- and β-1,4-linkages, dermatan sulfate has predominantly α-1,3- and β-1,4-linkages, and heparin/heparan sulfate have a mixture of (β-1,4- and α-1,4-linkages, wherein the primary repeating unit does not contain 3 or more α-1,4-linkages (Glycosaminoglycans and Proteoglycans, sigma.com/glycobiology), as required for cleavage by α-amylase.

A previous study discussed a method for treating wounds comprising the step of administering an effective amount of a carbohydrate-active enzyme, wherein such enzymes were preferentially chondroitinases, enzymes that catalyze the hydrolysis of the chondroitin chains on proteoglycans containing (1-4)-β-D- and (1-3)-β-D linkages, and hyaluronidases, enzymes that cleave hyaluronan, which contains β-1,4- and β-1,3-glycosidic bonds, with limited ability to degrade chondroitin and chondroitin sulfates (International Patent Publication Number WO1999046368).

The compositions and methods described herein pertain to the use of a non-protease hydrolytic enzyme for necrotic tissue debridement, where it was unexpectedly found that the family of amylases, which include α-amylase, β-amylase, and γ-amylase, was able to digest and decompose a neurotic tissue analog: boiled pig skin (U.S. Pat. No. 8,119,124), as well as, freshly excised rat skin.

Amylase is a digestive enzyme that aids in the cleavage of bonds in sugar residues in polysaccharides. It is found in two primary types in the human body: salivary amylase and pancreatic amylase. In saliva, salivary amylase is responsible for the breakdown of starch and glycogen into glucose, maltose, and dextrin. Pancreatic amylase further degrades starches in the digestive system.

In some embodiments, the non-proteolytic component is greater than the proteolytic component of the debridement composition. In some embodiments, a ratio of non-proteolytic enzymes to proteolytic enzymes in the debridement composition is at least 4:1, at least 5:1, or at least 10:1, at least 20:1 at least 40:1, at least 60:1, at least 80:1, or at least 100:1. Where the amount of proteolytic enzymes is 0 and the amount of non-proteolytic enzyme is greater than 0, the ratio is ∞:1. In some embodiments, the debridement composition comprises less than 0.01% by weight proteolytic enzymes, or less than 0.001% by weight of proteolytic enzymes, based on the total weight of the debridement composition. In some embodiments, the debridement composition comprises up to 20% by weight of proteolytic enzyme, or up to 15% by weight of proteolytic enzyme, or up to 10% by weight of proteolytic enzyme.

Relative to the three forms of amylase, α-amylase (also called 1,4-α-D-glucan glucanohydrolase) is an endoamylase that is found in all living organisms. It functions in a random manner by a multiple-attack mechanism on starch, glycogen and related polysaccharides and oligosaccharides with α-1,4-glycosidic linkages, ultimately yielding glucose and maltose, as well as, larger oligosaccharides, none of which are present in human skin, α-Amylase hydrolyzes 1,4-α-D-glucosidic linkages in polysaccharides that contain 3 or more 1,4-α-linked D-glucose units (Sigma Aldrich, http://www.sigmaaldrich.com/life-science/metabolomics/enzyme-explorer/learning-center/carbohydrate-analysis.html). However, α-amylase cannot hydrolyze α-1,6-bonds in glycogen and amylopectin.

β-Amylase (also called 1,4-α-D-glucan maltohydrolase) and γ-amylase (also called (amyloglucosidase, glucan 1,4-α-glucosidase, and glucoamylase) are exoamylases that are found exclusively in plants and microorganisms. Like α-amylase, β-amylase cannot hydrolyze 1,6-α-bonds. The β-amylase enzyme acts on the same substrates as α-amylase, but it removes successive maltose units from the non-reducing end. γ-Amylase releases β-D-glucose successively from the non-reducing end of the polysaccharide chains. Various forms of γ-amylase can hydrolyze 1,6-α-D-glucosidic bonds when the next bond in the sequence is a 1,4-bond, and some preparations can hydrolyze 1,6- and 1,3-α-D-glucosidic bonds in other polysaccharides. Combinations of the amylase enzymes are used in various preparations, such as food production, sweeteners, starch saccharification, brewing and distilling industries.

Calcium and chloride ions are essential for the activity of α-amylase. One $Ca^{2+}$ is tightly bound by each enzyme molecule, facilitating the proper conformation for hydrolytic activity, and chloride ions have been regarded as natural activators of the enzyme. Excess calcium stabilizes α-amylase towards heat. Catalytic activity is optimum at a temperature range between 40° C. and 45° C. and a pH of 7.0-7.5.

In this investigation, a novel composition for and approach to enzymatic debridement by amylase is considered through the cleavage of glycosidic bonds in and/or between glycosaminoglycan polysaccharides and collagen fibrils, and not by cleavage of peptide bonds of collagen, as has been done with previous enzymatic debridement products. The debriding formulation contains various types of the enzyme amylase. All amylases (α-, β-, γ-amylase) are a family of enzymes that preferentially hydrolyze the α-glycosidic bonds of polysaccharides, yielding lower molecular weight carbohydrate/sugar fragments. α-Amylase randomly cleaves the 1,4-α-D-glycosidic linkages between the adjacent glucose units in the linear amylose chain of starch. A significant benefit of α-amylase, is that it occurs naturally in humans and other mammals, and it is also found in plants, bacteria and fungi. In some embodiments, the amylase comprises a microbial amylase. Plant and animal sources can contain more harmful material than microbial based amylases, including phenolic compounds (from plants), endogenous enzyme inhibitors, and proteases.

Since amylase is not proteolytic, it does not self-digest in water, and is more stable compared to proteolytic enzymes under similar aqueous conditions. The high stability of amylase facilitates its storage in a hydrophilic formulation, which can be easily removed from a necrotic wound post-debridement, unlike petrolatum-based proteolytic debriding ointments.

The presence of amylase in proteolytic enzyme debridement has been reported primarily at a much lower quantity than proteases in these procedures, and often is an impurity in pancreatic, proteolytic enzymes (U.S. Pat. Nos. 3,409, 719; 8,540,983). A carbohydrate-active enzyme formulation based upon chondroitinases and hyaluronidases has been reported to debride burns and other wounds (International Patent Publication Number WO1999046368). It is anticipated that these enzymes presumably would be active against the proteoglycans associated with collagen in skin, such as the predominant proteoglycan of chondroitin sulfate. No report has discussed the enzymatic debridement of necrotic tissue based upon amylase as the principal enzymatic debriding agent because amylase is presumed to degrade only α-1,4-glycosidic bonds such as in starch, a carbohydrate not involved in the extracellular matrix.

Starch molecules are glucose polymers linked together by the α-1,4- and α-1,6-glycosidic bonds, consisting of linear amylose and branched amylopectin components. In order to make use of the carbon and energy stored in starch, amylase, as part of the human digestive system, cleaves starch at multiple points, converting starch into smaller sugars, which are eventually converted to glucose units. Because of the existence of two types of linkages, the α-1,4- and the α-1,6-glycosidic bonds, different structures are possible for starch molecules. An unbranched, single chain polymer with only the α-1,4-glucosidic bonds is called amylose. On the other hand, the presence of α-1,6-glucosidic linkages results in the branched glucose polymer of amylopectin. Another closely related compound functioning as the glucose storage in human and animal cells is called glycogen. Glycogen has a structure similar to that of amylopectin, except that the branches in glycogen tend to be shorter and more numerous. Neither amylose, nor amylopectin, nor glycogen is believed to be present in human or animal skin as a component of stabilizing or interacting with collagen of the extracellular matrix.

The specificity of the bond attacked by α-amylase depends on the source of the enzyme. Currently, two major classes of α-amylase are commercially produced through microbial fermentation. Based on where the cleavage occurs in the glucose polymer chain, the initial step in random depolymerization of starch is the splitting of large chains into various smaller sized segments. The breakdown of large segments drastically reduces the viscosity of the gelatinized starch solution, resulting in liquefaction because of the reduced viscosity of the solution. The final stage of the depolymerization is saccharification, which results predominantly in the formation of monosaccharides, disaccharides, and trisaccharides.

Because bacterial α-amylase randomly attacks only the α-1,4-bonds, it belongs to the liquefying category. On the other hand, the fungal α-amylase belongs to the saccharifying category and attacks the second linkage from the nonreducing terminals (i.e., C4 end) of the straight segment, resulting in the splitting off of two glucose units at a time, giving the disaccharide maltose. The bond breakage is thus more extensive in saccharifying enzymes than in liquefying enzymes. The starch chains are literally chopped into small bits and pieces. Finally, γ-amylase selectively attacks the last bond on the nonreducing terminals and can act on both the α-1,4- and the α-1,6-glucosidic linkages at a relative rate of 1:20, resulting in the splitting off of simple glucose units into the solution, α-Amylase and γ-amylase may be used together to convert starch to simple sugars.

Amylase has also been used in the cleaning of hard surfaces and fabrics, as described in International Patent Publication Number WO 2007/144856, which include all-purpose or "heavy-duty" washing agents, especially laundry detergents; liquid, gel or paste-form all-purpose washing agents, especially the so-called heavy-duty liquid types; liquid fine-fabric detergents; hand dishwashing agents or light duty dishwashing agents, especially those of the high-foaming type; machine dishwashing agents, including the various tablet, granular, liquid and rinse-aid types for household and institutional use; liquid cleaning and disinfecting agents, including antibacterial hand-wash types, laundry bars, mouthwashes, denture cleaners, car or carpet shampoos, bathroom cleaners; hair shampoos and hair-rinses; shower gels and foam baths and metal cleaners; as well as cleaning auxiliaries such as bleach additives and "stain-stick" or pre-treat types.

Amylases are one of the main enzymes used in industry. Amylases have potential application in a wide number of industrial processes such as food, fermentation and pharmaceutical industries. Although α-amylases can be obtained from plants, animals and microorganisms, enzymes from fungal and bacterial sources have dominated applications in industry, including microorganisms of *Bacillus* spp. and *Aspergillus* spp., with most commercial amylases being produced from bacterial sources such as *Bacillus licheniformis, Bacillus amyloliquefaciens, Bacillus subtilis*, or *Bacillus stearothermophilus*.

The debridement compositions described herein can be formulated as a liquid, gel, powder, paste, ointment, lotion, emulsion, or microemulsion, and can be delivered to necrotic or devitalized tissue as a foam, spray, dressing, mesh, bandage, or film, wherein the latter may contain film-forming polymers, semi-permeable or permeable polymers, or a degradable or non-degradable substrate, such as a dressing, bandage, or foamed material. The debridement composition can include one or more pharmaceutically or cosmetically acceptable carrier that is compatible with the enzymatic debridement composition. Examples of pharmaceutically or cosmetically acceptable carriers include, but are not limited to, water, normal saline (isotonic saline), Dulbecco's phosphate buffered saline (DPBS), phosphate buffered saline (PBS), saline solutions containing added calcium chloride, Ringer's solution, glycerin, propylene glycol, ethanol, isopropanol, butane-1,3-diol, liquid poly (alkylene glycol)s (e.g., poly(ethylene glycol), methyl ether-terminated poly(ethylene glycol), poly(ethylene glycol-block-propylene glycol-block-ethylene glycol)), and water-soluble liquid silicone polyethers, water-insoluble media, such as, isopropyl myristate, isopropyl palmitate, mineral oil, dimethicone, and petrolatum. In some embodiments, excipients can be present in an amount ranging from 0% to 99.9 wt % based on the weight of the debridement composition.

The debridement composition can also include wetting agents, buffers, gelling agents, surfactants, chelating agents and emulsifiers. Other excipients could include various water-based buffers ranging in pH from 5.0-7.5, silicones, polyether copolymers, vegetable and plant fats and oils, essential oils, hydrophilic and hydrophobic alcohols, vitamins, monoglycerides, and penetration enhancement esters such as laurate esters, myristate esters, palmitate esters, and stearate esters. In some embodiments, the debridement composition can be in a form selected from liquid, gel, paste, cream, emulsion, and combinations thereof, and the like.

In some embodiments, the enzymatic debridement composition is lyophilized to a dry powder. The lyophilized enzymatic debridement composition may be used in powder form, or the powder may be further processed into solutions, creams, lotions, gels, sprays, foams, aerosols, films, or other formulations.

In some embodiments, surfactant emulsifiers can be used to form emulsions, which facilitate compatibilization with organic solvents. Examples of organic solvents include, but are not limited to, non-stinging solvents, such as volatile silicone solvents and volatile alkanes to form water-in-oil or oil-in-water emulsions, reverse emulsions, miniemulsions (nanoemulsions), microemulsions, and reverse microemulsions. Non-stinging volatile silicone solvents include, but are not limited to low molecular weight polydimethylsiloxanes, such as hexamethyldisiloxane or octamethyltrisiloxane; low molecular weight cyclic siloxanes, such as hexamethylcyclotrisiloxane or octamethylcyclotetrasiloxane; linear, branched or cyclic alkanes, such as propane, butane, and isobutane (aerosols under pressure), pentane, hexane, heptane, octane, isooctane, and isomers thereof, petroleum distillates, and cyclohexane; and chlorofluorocarbons, such as, trichloromonofluoromethane, dichlorodifluoromethane, and dichlorotetrafluoroethane; fluorocarbons, such as tetrafluoroethane, heptafluoropropane, 1,1-difluoroethane, pentafluoropropane, perfluoroheptane, perfluoromethylcyclohexane; hydrofluoroalkanes, such as aerosols of 1,1,1,2,-tetrafluoroethane and 1,1,1,2,3,3,3-heptafluoropropane, combinations thereof and the like; and volatile gases under pressure, such as air, nitrous oxide, and liquid carbon dioxide; or a mixture thereof. As will be understood, when stored under high pressure, carbon dioxide can be present in the form of a liquid at room temperature. In some embodiments, the volatile solvent can be hexamethyldisiloxane, isooctane, and mixtures thereof. In some embodiments, the volatile solvent can be hexamethyldisiloxane. In some embodiments, solvents can be present in an amount ranging from 0% to 99.9 wt % based on the weight of the debridement composition.

Water-soluble viscosity builders useful herein include, but are not limited to, methylcellulose, hydroxyethylcellulose, hydroxypropylcellulose, hydroxypropylmethylcellulose, carboxymethylcellulose, guar gum, hydroxyethylguar, hydroxypropylguar, hydroxypropylmethylguar, carboxymethylguar, carboxymethylchitosan, locust bean gum, carrageenan, xanthan gum, gellan gum, Aloe vera gel, sclerog-lucan, schizophyllan, gum arabic, tamarind gum, poly(vinyl alcohol), poly(ethylene oxide), poly(ethylene glycol), poly (methyl vinyl ether), Carbomer and its salts, poly(acrylic acid) and its salts, poly(methacrylic acid) and its salts, sodium poly(2-acrylamido-2-methylpropanesulfonate), polyacrylamide, poly(N,N-dimethylacrylamide), poly(N-vinylacetamide), poly(N-vinylformamide), poly(2-hydroxyethyl methacrylate), poly(glyceryl methacrylate), poly(N-vinylpyrrolidone), poly(N-isopropylacrylamide) and poly (N-vinylcaprolactam), the latter two hydrated below their Lower Critical Solution Temperatures, and the like, and combinations thereof.

In some embodiments, water-soluble polymers that are neutral in charge and are not enzymatically degradable by amylase can be used as viscosity builders. Examples of such viscosity builders include, but are not limited to, poly (ethylene oxide), poly(ethylene glycol), poly(vinyl alcohol), and poly(N-vinylpyrrolidone). Other viscosity builders useful in the debridement compositions described herein include, but are not limited to neutral polysaccharides that have β-linkages between monosaccharide units, such as in methylcellulose, hydroxyethylcellulose, hydroxypropylcellulose, hydroxypropylmethylcellulose. Still other viscosity builders useful in the debridement compositions described herein include, but are not limited to, those that are anionic in charge, such as Carbomer and its salts, poly(acrylic acid) and it salts, and poly(methacrylic acid) and its salts. Still other viscosity builders are anionic polysaccharides that have β-linkages between monosaccharide units, such as in carboxymethylcellulose. Such viscosity builders may be employed in amounts ranging from about 0.01 to about 50.0 weight percent of the debridement composition for preparation of viscous gels or pastes. Viscosity builders can be present in amounts ranging from 0.1 to 45% by weight, from 0.5 to 25% by weight, or from 1.0 to 10.0% by weight.

Essential oils can also be added to the formulation as fragrance or aromatic agents, and/or as antimicrobial agents. Examples of essential oils useful in the debridement compositions described herein include, but are not limited to, thymol, menthol, sandalwood, camphor, cardamom, cinnamon, jasmine, lavender, geranium, juniper, menthol, pine, lemon, rose, eucalyptus, clove, orange, oregano, mint, linalool, spearmint, peppermint, lemongrass, bergamot, citronella, cypress, nutmeg, spruce, tea tree, wintergreen (methyl salicylate), vanilla, and the like. In some embodiments, the essential oils can be selected from thymol, sandalwood oil, wintergreen oil, eucalyptol, pine oil, and combinations thereof. In some embodiments, essential oils can be present in an amount ranging from 0% to 5 wt % based on the weight of the debridement composition. In some embodiments, essential oils can be present in an amount of at least 0.1 wt %, or at least 0.25 wt %, or at least 0.5 wt % based on the weight of the debridement composition.

In some embodiments, chlorophyllin, a water-soluble semi-synthetic derivative of chlorophyll, may also be used to control wound odor and to provide anti-inflammatory properties. In some embodiments, chlorophyllin can be present in an amount ranging from 0% to 5 wt % based on the weight of the debridement composition. In some embodiments, chlorophyllin can be present in an amount of at least 0.1 wt %, or at least 0.25 wt %, or at least 0.5 wt % based on the weight of the debridement composition.

A keratolytic agent can also be added to the debridement composition to aid in digesting the eschar tissue. For example, the keratolytic agent can promote the softening and peeling of the epidermis. Keratolytic agents useful in the debridement compositions as described herein include, but are not limited to, urea, salicylic acid and α-hydroxyacids, such as lactic acid, glycolic acid, and citric acid. For example, urea can be used to help remove dead tissue in necrotic wounds to help wound healing (U.S. Pat. No. 8,754,045). In some embodiments, the keratolytic agent can be present in an amount ranging from 0% to 15 wt % based on the weight of the debridement composition. In some embodiments, essential oils can be present in an amount of at least 0.1 wt %, or at least 0.25 wt %, or at least 0.5 wt % based on the weight of the debridement composition.

In some embodiments, the total amount of non-proteolytic enzyme in a debridement composition capable of debriding devitalized or necrotic tissue can be at least 0.001 wt % to 60 wt % based on the total weight of the debridement composition. In some embodiments, the total amount of non-proteolytic enzyme can be at least 1 wt % to 50 wt %, or at least 2 wt % to 40 wt %, or at least 5 wt % to 35 wt %, or at least 10 wt % to 30 wt %. In some embodiments, the non-proteolytic enzyme is an amylase. In some embodiments, the non-proteolytic enzyme is α-amylase.

In some embodiments, the amount of non-proteolytic enzymatic debridement component capable of debriding devitalized or necrotic tissue in the debridement composition can be 100 wt %, or at least 99.5 wt %, or at least 99 wt %, or at least 95 wt %, or at least 90 wt %, or at least 85 wt %, or at least 80 wt %. In some embodiments, the amount of non-proteolytic enzymatic debridement component capable of debriding devitalized or necrotic tissue in the debridement composition can be up to 100 wt %, or up to 99.5 wt %, or up to 99 wt %, or up to 95 wt %, or up to 90 wt %, or up to 85 wt %, or up to 80 wt %. In some embodiments, the amount of non-proteolytic enzymatic debridement component capable of debriding devitalized or necrotic tissue in the debridement composition can be at least 0.001 wt %, or at least 0.01 wt %, or at least 0.05 wt %, or at least 0.075 wt %, or at least 0.1 wt %, or at least 0.15 wt %.

In some embodiments, the amount of amylase in the debridement composition can be 100 wt %, at least 99.5 wt %, at least 99 wt %, at least 95 wt %, at least 90 wt %, at least 85 wt %, or at least 80 wt %. In some embodiments, the amount of amylase in the non-proteolytic enzymatic debridement component can be 100 wt %, at least 99.5 wt %, at least 99 wt %, at least 95 wt %, at least 90 wt %, at least 85 wt %, or at least 80 wt %, with the remainder of the non-proteolytic enzymatic debridement component being other non-proteolytic enzymes. The amount of α-amylase can be at least 10 wt %, at least 20 wt %, at least 30 wt %, at least 40 wt %, at least 50 wt %, at least 60 wt %, at least 70 t-%, at least 80 wt %, at least 90 wt %, or 100 wt % of the amylase content. In some embodiments, the remaining portion of the non-proteolytic enzymatic debridement component (20 wt % or less, 15 wt % or less, 10 wt % or less, 5 wt % or less, 1 wt % or less, 0.5 wt % or less) can be, but not limited to, hydrolytic, lytic, and oxidative/reductive enzymes including, but not limited to, hydrolytic, lytic, and oxidative/reductive enzymes selected from the group consisting of lipases, hyaluronidases, chondroitinases, heparanases, heparinases, peroxidases, xylanases, nucleases, phospholipases, esterases, phosphatases, isoamylases, maltases, glycosylases, galactosidases, cutinases, lactases, inulases, pectinases, mannanases, glucosidases, invertases, pectate lyases, reductases, oxidases, phenoloxidases, lipoxygenases, ligninases, pullulanases, tannases, pentosanases, glucanases, arabinosidases, sulfatases, cellulases, hemicellulases, laccases, mixtures thereof, and the like.

Examples of proteolytic enzymes that can be present in the debridement composition include, but are not limited to, proteases and keratinases.

The debridement composition can include an aqueous media. In some embodiments, the aqueous media can have a pH in the range 3.0-10.0, or from 4.5-8.0, or from 5.5 to 7.5. in some embodiments, the debridement composition can have an osmolality of 10-340 mOsm/kg. Where the debridement composition is an aqueous-based solution, gel or paste, a water-soluble polymer can be added to increase solution viscosity and to prolong residence time of the enzymatic composition on the necrotic tissue, on the surface of a wound, or subcutaneously in a wound.

The enzymatic debridement composition can be applied to the devitalized tissue as needed to dissolve necrotic debris in and around a wound. For example, in some embodiments the enzymatic debridement composition can be in contact with the devitalized tissue for about 1 to 48 hours, 1 to 24 hours, 1 to 12 hours, 1 to 8 hours, 1 to 4 hours, or 1 to 2 hours before removal.

In some embodiments, the amylase formulation can be removed from a wound by wiping or by rinsing with saline or water. These steps may be repeated as needed. A wide variety of wounds can be treated with the debridement compositions described herein, including full and partial thickness burn wounds, diabetic ulcers, ulcerative lesions, principally pressure (decubitus) ulcers, venous ulcers, trophic ulcers, surgical wounds such as amputation, incisional, traumatic and pyogenic wounds, infected wounds by microorganisms, donor and receptor skin graft wounds, malignancy, cysts, radiation wounds, sunburn, and frostbite.

In some embodiments, the enzymatic debridement composition can be injected into the devitalized tissue. A penetration enhancer may also be utilized to enhance transdermal delivery of solutions, gels, creams, lotions, aerosols, and sprays. Penetration enhancers that can be used in the debridement compositions described herein include, but are not limited to, fatty acids such as branched and linear $C_6$-$C_{16}$ saturated acids, unsaturated acids, such as $C_{14}$ to $C_{22}$, oleic acid, cis-9-octadecenoic acid, linoleic acid, linolenic acid, fatty alcohols, such as saturated $C_8$-$C_{18}$ terpenes, such as d-limonene, α-pinene, 3-carene, menthone, fenchone, pulegone, piperitone, eucalyptol, chenopodium oil, carvone, menthol, α-terpineol, terpinen-4-ol, carveol, limonene oxide, pinene oxide, cyclopentane oxide, triacetin, cyclohexane oxide, ascaridole, 7-oxabicylco[2,2,1]heptane, 1,8-cineole, glycerol monoethers, glycerol monolaurate, glycerol monooleate, isostearyl isostearate, isopropyl myristate, isopropyl palmitate, isopropyl lanolate, pyrrolidones, such as N-methyl-2-pyrrolidone, 1-ethyl-2-pyrrolidone, 5-methyl-2-pyrrotidone, 1,5-dimethyl-2-pyrrolidone, 2-pyrrolidone-5-carboxylic acid, N-hexyl-2-pyrrolidone, N-lauryl-2-pyrrolidone, 1-dodecylazacycloheptan-2-one, 4-decyloxazolidin-2-one, N-dodecylcaprolactam, and 1-methyl-3-dodecyl-2-pyrrolidone N-n-butyl-N-n-dodecylacetamide, N,N-di-n-dodecylacetamide, N-cycloheptyl-N-n-dodecylacetamide and N,N-di-n-propyldodecanamide, urea, 1-dodecylurea, 1,3-didodecylurea, 1,3-diphenyl urea, dimethyl sulfoxide, decylmethyl sulfoxide, tetradecylmethyl sulfoxide, cyclodextrins, and combinations thereof. Also effective penetration enhancers include 1-alkyl-2-piperidinones, 1-alkyl-2-azacycloheptanones, such as 1-dodecyazacycloheptan-2-one, 1,2,3-alkanetriols, such as 1,2,3-nonanetriol, 1,2-alkanediols, n-, 2-(1-alkyl)-2-methyl-1,3-dioxolanes, oxazolidinones, such as 4-decyloxazolidin-2-one, N,N-dimethylalkanamides, 1,2-dihydroxypropyl alkanoates, such as 1,2-dihydroxypropyl decanoate, 1,2-dihydroxypropyl octanoate, sodium deoxycholate, trans-3-alken-1-ols, cis-3-alken-1-ols, and trans-hydroxyproline-N-alkanamide-C-ethylamide, and combinations thereof. In some embodiments, the penetration enhancers can include hydrophobic esters isopropyl myristate, isopropyl palmitate, or combinations thereof.

Because of the possibly of infection in devitalized necrotic tissue, the debridement composition can include a biological agent in an amount sufficient to hinder or eradicate microorganisms. Such biological agents include, but are not limited to, antibiotics, antiseptics, anti-infective agents, antimicrobial agents, antibacterial agents, antifungal agents, antiviral agents, antiprotozoal agents, sporicidal agents, antiparasitic agents. In some embodiments, the biological agent is biodegradable and non-cytotoxic to human and animal cells. Useful biocidal agents include, but are not limited to, biguanides, such as poly(hexamethylene biguanide hydrochloride) (PHMB), a low molecular weight synthetic polycation, chlorhexidine and its salts, such as chlorhexidine digluconate (CHG), and alexidine and its salts, where the latter two are bis(biguanides).

In some embodiments, the biguanide is PHMB because of its high biocidal activity against microorganisms, combined with its biodegradation and low cytotoxicity. PHMB is primarily active against Gram negative and Gram positive bacteria, fungi, and viruses, and also serves as a preservative. In contrast to antibiotics, which are considered regulated pharmaceutical drugs, to which bacterial resistance can occur, such resistance does not occur with PHMB. In general, an antimicrobial agent is defined as a substance that kills microorganisms or inhibits their growth or replication, while an anti-infective agent is defined as a substance that counteracts infection by killing infectious agents, such as microorganisms, or preventing them from spreading. Often, the two terms are used interchangeably. As used herein, PHMB is considered an antimicrobial agent.

In some embodiments, the debridement composition is an aqueous debridement composition. In some embodiments, aqueous debridement compositions described herein can include biocidal PHMB at a concentration ranging from 0.01 wt % (100 ppm) to 1 weight % (10,000 ppm), or ranging from 0.05 wt % (500 ppm) to 0.5 wt % (5,000 ppm), or ranging from 0.1 wt % (1,000 ppm) to 0.15 wt % (1,500 ppm) based on the total weight of the debridement composition. Bis(biguanides), such as alexidine and its salts and chlorhexidine and its salts, can also be added to the antimicrobial compositions in concentrations from 0.001 wt % (10 ppm) to 4.0 wt % (40,000 ppm).

The interaction of low molecular weight PHMB polycation (molecular weight 2,400 Daltons) with amylase, a negatively charged, high molecular weight amylase (molecular weight 55,000 Daltons) at physiological pH can generate a protein-polyelectrolyte complex of PHMB ionically interacted with amylase. In a wound, PHMB may be released from the protein-polyelectrolyte complex in a continuous release fashion as a function of the amount of low molecular weight cation in bodily fluids (such as sodium, potassium, calcium and magnesium ions) displacing the cationic PHMB ionic interaction with anionic amylase sites.

The dosage at which the therapeutic amylase compositions are administered is dependent upon the source of the amylase, the activity (i.e., the number of Units involved), the size of necrotic tissue, the age of the patient, the availability of clinical care, and the incidence of infection. The amount of therapeutic amylase that may be administered up to twice per day can range from application of a powder (at 100 wt %) to a dilute solution (of about 0.001 wt %). In some embodiments, the activity of the amylase can range from 250 Units to 250,000 Units per gram of enzyme in 1 gram of the debridement composition.

The debriding composition on necrotic tissue can be performed by a clinician, such that the patient is not in any further medical difficulty. The amylase method of debridement can be performed in combination with other known debriding methods.

As used herein, "debridement" has its standard meaning and includes the removal of lacerated, devitalized, dead, damaged, infected or contaminated tissue, foreign bodies, and other debris from the wound bed in order to expose healthy tissue. Nonviable or necrotic tissue can either be eschar or slough.

As used herein, "necrotic tissue" has its standard meaning and includes dead tissue that contains dead cells and debris, as a consequence of the fragmentation of dying cells. The color of necrotic tissue changes from red to brown, or black or purple, as it becomes more dehydrated, finally resulting in a black, dry, thick, and leathery eschar structure, which can occur in a wide variety of wound types, including burns and all types of chronic wounds.

As used herein, "eschar" has its standard meaning and includes forms of necrotic tissue. It is the leather-like covering on the wound at the skin surface, and it can be either hard or pliable.

As used herein, "slough" has its standard meaning and includes moist necrotic tissue. This type of devitalized tissue is soft, moist and often stringy in consistency and is usually yellow, white or grey in color.

As used herein, "devitalized tissue" has its standard meaning and includes tissue devoid of vitality or life, that is, dead tissue.

As used herein, "proteolytic enzyme" has its standard meaning and includes enzymes that independently cleave (digest, break, hydrolyze) the long chainlike polymer molecules of proteins into shorter fragments of peptides and, eventually, into their basic components of amino acids.

As used herein, "excise" has its standard meaning and includes a surgical procedure requiring incision utilizing a scalpel or other sharp instrument through the deep dermis (including subcutaneous and deeper tissues).

As used herein, a covalent bond that is formed between a carbohydrate molecule and another molecule, particularly between two monosaccharide moieties, is a "glycosidic bond" or "glycodisic linkage."

As used herein, "α-1,4-glycosidic linkages" are bonds that are normally formed between the carbon-1 on one sugar and the carbon-4 on another sugar moiety in a polysaccharide. An α-glycosidic bond is formed when the —OH group on carbon-1 is below the plane of the glucose ring. On the other hand, a β-glycosidic bond is formed when it is above the plane. For example, cellulose is formed of glucose molecules linked by 1-4 β-glycosidic bonds, whereas starch is composed of 1-4 α-glycosidic bonds.

As used herein, "α-amylase" includes naturally occurring α-amylases as well as recombinant α-amylases, wherein recombinant α-amylase means an α-amylase in which the DNA genetic sequence encoding the naturally occurring α-amylase is modified to produce a mutant DNA sequence that encodes the substitution, insertion or deletion of one or more amino acids in the α-amylase sequence compared to the naturally occurring α-amylase.

As used herein, "amylolytic" is characterized by or capable of the enzymatic digestion of starch into dextrins and sugars, particularly by amylase.

As used herein, the amount of enzyme utilized is expressed in weight percent and its activity is given in Units of activity per gram, where a "Unit" is defined as the amount of enzyme that catalyzes the conversion of 1 micromole of substrate per minute.

As used herein, "surfactant" has its standard meaning and includes compounds that lower the surface tension (or interfacial tension) between two liquids or between a liquid and a solid and includes emulsifying agents, emulsifiers, detergents, wetting agents, and surface-active agents.

As used herein, "microemulsion" has its standard meaning and includes thermodynamically stable mixtures of oil, water (and/or hydrophilic compound) and surfactant. Microemulsions include three basic types: direct (oil dispersed in water, o/w), reverse (water dispersed in oil, w/o) and bicontinuous. Microemulsions are optically clear because the dispersed micelles have a diameter that is less than the wavelength of visible light (e.g., less than 380 nanometers, less than 200 nanometers, or less than 100 nanometers) in diameter. In the absence of opacifiers, microemulsions are optically clear, isotropic liquids.

As used herein, "reverse microemulsion" has its standard meaning and includes a microemulsion comprising a hydrophilic phase suspended in a continuous oil phase. A reverse microemulsion can include droplets of a hydrophilic phase (e.g., water, alcohol, or a mixture of both) stabilized in an oil phase by a reverse emulsion surfactant. In such instances, a hydrophilic active agent can be solubilized in the droplets. However, in other instances, the reverse microemulsion can be free of water and/or alcohol, and the hydrophilic active agent can be directly solubilized in the oil phase by the reverse emulsion surfactant.

As used herein, "hydrophilic" has its standard meaning and includes compounds that have an affinity to water and can be ionic or neutral or have polar groups in their structure that attract water. For example, hydrophilic compounds can be miscible, swellable or soluble in water.

As used herein, "aqueous" compositions refer to a spectrum of water-based solutions including, but not limited to, homogeneous solutions in water with solubilized components, emulsified solutions in water stabilized by surfactants or hydrophilic polymers, and viscous or gelled homogeneous or emulsified solutions in water.

As used herein, an enzyme is "soluble" or "solubilized" if the amount of enzyme present in the solvent system is dissolved in the solvent system without the enzyme forming a precipitate or visible, swollen gel particles in solution.

As used herein, "non-stinging" means that the formulation does not cause a sharp, irritatingly, burning or smarting pain as a result of contact with a biological surface.

As used herein, "volatile" has its standard meaning, that is, it can evaporate rapidly at normal temperatures and pressures. For example, a solvent is volatile if one drop (0.05 mL) of the solvent will evaporate completely between 20-25° C. within 5 minutes, or within 4 minutes, or within 3 minutes, or within 2 minutes, or within 1 minute, or within 30 seconds, or within 15 seconds.

As used herein, an "antimicrobial agent" is defined as a substance that kills microorganisms or inhibits their growth or replication, while an anti-infective agent is defined as a substance that counteracts infection by killing infectious agents, such as microorganisms, or preventing them from spreading. Often, the two terms are used interchangeably. Antibiotics are considered those substances that were originally produced by a microorganism or synthesized with active properties that can kill or prevent the growth of another microorganism. The term antibiotic is commonly used to refer to almost any prescribed drug that attempts to eliminate infection. Antimicrobial agents do not cause biocidal resistance such as can occur with antibiotics, wherein antibiotic resistance to a drug can occur. Antimicrobial agents have a broad spectrum of activity against bacteria, fungi, viruses, protozoa and prions. Examples of antimicrobial agents include biguanides, such as poly(hexamethylene biguanide hydrochloride) (PHMB), chlorhexidine and its salts, alexidine and its salts, povidoneliodine, cadexomer iodine, silver sulfadiazine, nanocrystalline silver, ionic silver, honey, dilute bleaching agents such as sodium hypochlorite and hypochlorous acid, hydrogen peroxide, organic peroxides such as benzoyl peroxide, alcohols such as ethanol and isopropanol, anilides such as triclocarban, bisphenols such as triclosan, chlorine compounds such as chlorine dioxide and N-chloramines, and quaternary ammonium compounds such as benzalkonium chloride, benzethonium chloride, cetyltrimethylammonium chloride, cetylpyridinium chloride, and alkyltrimethylammonium bromides, as well as miconazole, clotrimazole, ketoconazole, fluconazole, crystal violet, amphotericin B, tee tree oil, and the like. Biguanides, such as PHMB, are useful in the debridement compositions described herein.

A polymeric biguanide useful in the debridement compositions described herein is poly(hexamethylene biguanide), commercially available from Arch Chemicals, Inc., Smyrna, Ga. under the trademark Cosmocil™ CQ. Poly (hexamethylene biguanide) polymers are also referred to as poly(hexamethylene biguanide) (PHMB), poly(hexamethylene bisbiguanide) (PHMB), poly(hexamethylene guanide) (PHMB), poly(aminopropyl biguanide) (PAPB), poly [aminopropyl bis(biguanide)](PAPB), polyhexanide and poly(iminoimidocarbonyl)iminohexamethylene hydrochloride; however, PHMB is the preferred abbreviation. PHMB is a broad spectrum antimicrobial and has been used in contact lens multipurpose solutions, wound rinsing solutions, wound dressings, perioperative cleansing products, mouthwashes, surface disinfectants, food disinfectants, veterinary applications, cosmetic preservatives, paper preservatives, secondary oil recovery disinfectants, industrial water treatments, and in swimming pool cleaners. It is normally obtained commercially in the hydrochloride form in water. Other antimicrobial polymers can also be added, such as polyquaternium 1, polyquaternium 6, polyquaternium 10, cationic guar, and water-soluble derivatives of chitosan.

As used herein, an "antibiotic" is a medicine or drug, usually prescribed, such as penicillin, streptomycin, chloramphenicol, and tetracycline, usually produced by various microorganisms, that inhibits the growth of or destroys microorganisms, used primarily in the treatment of infectious disease. Antibiotics are considered those substances that were originally produced by a microorganism or synthesized with related active properties that can kill or prevent the growth of another microorganism. The term antibiotic is commonly used to refer to almost any prescribed drug that attempts to eliminate infection.

As used herein, "antibiotic resistance" is the ability of bacteria and other microorganisms to resist the effects of an antibiotic to which they were once susceptible.

The debridement composition described herein can include a biocidal monoalkyl glycol, glycerol alkyl ether, and monoacyl glycerol at a combined concentration of from 0.05 wt % (500 ppm) to 4 wt % (4,000 ppm), or from 0.1 wt % (1,000 ppm) to 1 wt % (10,000 ppm), or from 0.4 wt % (4,000 ppm) to 0.6 wt % (6,000 ppm) based on the weight of the debridement composition. The monoalkyl glycol, glycerol alkyl ether, and monoacyl glycerol can be hydrophobic.

Examples of monoalkyl glycols useful in the debridement compositions described herein include, but are not limited to, 1,2-propanediol (propylene glycol), 1,2-butanediol, 1,2-pentanediol, 1,2-hexanediol, 1,2-heptanediol, 1,2-octanediol (caprylyl glycol), 1,2-nonanediol, 1,2-decanediol, 1,2-undecanediol, 1,2-dodecanediol, 1,2-tridecanediol, 1,2-tetradecanediol, 1,2-pentadecanediol, 1,2-hexadecanediol, 1,2-heptadecanediol and 1,2-octadecanediol. Non-vicinal glycols can also be added to enhance biocidal activity. Exemplary, non-vicinal glycols include, but are not limited to, 2-methyl-2,4-pentanediol, 1,3-butanediol, diethylene glycol, triethylene glycol, and glycol bis(hydroxyethyl) ether.

Examples of glycerol alkyl ethers useful in the debridement compositions described herein include, but are not limited to, 1-O-heptylglycerol, 1-O-octylglycerol, 1-O-nonylglycerol, 1-O-decylglycerol, 1-O-undecyiglycerol, 1-O-dodecylglycerol, 1-O-tridecylglycerol, 1-O-tetradecylglycerol, 1-O-pentadecylglycerol, 1-O-hexadecylglycerol (chimyl alcohol), 1-O-heptadecylglycerol, 1-O-octadecylglycerol (batyl alcohol), 1-O-octadec-9-enyl glycerol (selachyl alcohol), glycerol 1-(2-ethylhexyl) ether (also known as octoxyglycerin, 2-ethythexyl glycerin, 3-(2-ethylhexyloxy)propane-1,2-diol, and Sensiva® SC 50), glycerol 1-heptyl ether, glycerol 1-octyl ether, glycerol 1-decyl ether, and glycerol 1-dodecyl ether, glycerol 1-tridecyl ether, glycerol 1-tetradecyl ether, glycerol 1-pentadecyl ether, glycerol 1-hexadecyl ether and glycerol 1-octadecyl ether.

Examples of monoacyl glycerols useful in the debridement compositions described herein include, but are not limited to, 1-O-decanoylglycerol (monocaprin), 1-O-undecanoylglycerol, 1-O-undecenoylglycerol, 1-O-dodecanoylglycerol (monolaurin, also called glycerol monolaurate and Lauricidin®), 1-O-tridecanoylglycerol, 1-O-tetradecanoylglycerol (monomyristin), 1-O-pentadecanoylglycerol, 1-O-hexadecanoylglycerol, 1-O-heptadecanoylglycerol, and 1-O-octanoylglycerol (monocaprylin). In general, glycerols substituted in the 1-O-position are more preferred than those substituted in the 2-O-position, or disubstituted in the 1-O and 2-O positions.

As used herein, "hydrophobic" refers to repelling water, being insoluble or relatively insoluble in water, and lacking an affinity for water. Hydrophobic compounds with hydrophilic substituents, such as vicinal diols, may form emulsions in water, with or without added surfactant.

As used herein, "amphoteric" refers to a mixture of cationic and anionic charges on a molecule or polymer in which overall charge is locally pH dependent, whereas "ampholytic" has an equal number of cationic and anionic charges over a broad pH range.

As used herein, an "excipient" is a usually inert substance that forms a vehicle, such as a liquid, fluid, or gel, that solubilizes or disperses an enzyme or other added ingredients. The amylase compositions can include one or more additional surfactants to enhance necrotic tissue removal. Suitable surfactants include, but are not limited to, cationic, anionic, nonionic, amphoteric and ampholytic surfactants. In some embodiments, the surfactants are nonionic and amphoteric surfactants. In some embodiments, the surfactant can be present in an amount ranging from 0% to 10 wt % based on the weight of the debridement composition. In some embodiments, the surfactant can be present in an amount of at least 0.01 wt %, or at least 0.1 wt %, or at least 0.25 wt %, or at least 0.5 wt %, or at least 1 wt %, based on the weight of the debridement composition. The surfactants can have an HLB (hydrophilic-lipophilic balance) value of 18-30 in order to maintain the enzymes' catalytic structure in solution as well as not hindering the biocidal activity of any added antimicrobial agents, while facilitating a non-cytotoxic solution. The high values of the HLB represent surfactants that are more hydrophilic than those with lower HLB values.

Suitable nonionic surfactants include, but are not limited to, the ethylene oxide/propylene oxide block copolymers of poloxamers, reverse poloxamers, poloxamines, and reverse poloxamines. Poloxamers and poloxamines are preferred, and poloxamers are most preferred. Poloxamers and poloxamines are available from BASF Corp. under the respective trade names of Pluronic® and Tetronic®. Suitable Pluronic surfactants comprise but are not limited to Pluronic F38 having a HLB of 31, Pluronic F68 having a HLB of 29, Pluronic 68LF having a HLB of 26, Pluronic F77 having a HLB of 25, Pluronic F87 having a HLB of 24, Pluronic F88 having a HLB of 28, Pluronic F98 having a HLB of 28, Pluronic F108 having a HLB of 27, Pluronic F127 (also known as Poloxamer 407) having a HLB of 18-23, and Pluronic L35 having a HLB of 19. An exemplary poloxamine surfactant of this type is Tetronic 1107 (also known as Poloxamine 1107) having an HLB of 24.

In addition to the above, other neutral surfactants may be added, such as for example polyethylene glycol esters of fatty acids, e.g., coconut, polysorbate, polyoxyethylene or polyoxypropylene ethers of higher alkanes ($C_{12}$-$C_{18}$), polysorbate 20 available under the trademark Tween 20, polyoxyethylene (23) lauryl ether available under the trademark Brij 35, polyoxyethylene (40) stearate available under the trademark Myrj 52, and polyoxyethylene (25) propylene glycol stearate available under the trademark Atlas G 2612, all available by Akzo Nobel, Chicago, Ill. Other neutral surfactants include nonylphenol ethoxylates such as nonylphenol ethoxylates, Triton X-100, Brij surfactants of polyoxyethylene vegetable-based fatty ethers, Tween 80, decyl glucoside, and lauryl glucoside.

Amphoteric surfactants suitable for use in antimicrobial compositions according to the present invention include materials of the type offered commercially under the trademark Miranol (Rhodia). Another useful class of amphoteric surfactants is exemplified by betaines, including cocoamidopropyl betaine, undecylenamidoalkylbetaine, and lauramidoalkylbetaine and sodium cocoamphoacetate. Amphoteric surfactants are very mild and have excellent dermatological properties, making them particularly suited for use in personal care applications.

The debridement composition may further comprise a chelating agent at a concentration of from 0.01 weight % to 1 weight %. For example, the chelating agent can be present in an amount of at least 0.01 wt %, or at least 0.03 wt %, or at least 0.05 wt %, or at least 0.1 wt %, or at least 0.50 wt %, or at least 0.75 wt %, or at least 1.0 wt %. The chelating agent can be selected from the group that includes, but is not limited to, ethylenediaminetetraacetic acid (EDTA), nitrilotriacetic acid, nitrilotripropionic acid, diethylenetriaminepentaacetic acid, 2-hydroxyethylethylenediaminetriacetic acid, 1,6-diaminohexamethylenetetraacetic acid, 1,2-diaminocyclohexanetetraacetic acid. O,O'-bis(2-aminoethyl) ethyleneglycoltetraacetic acid, 1,3-diaminopropanetetraacetic acid, N,N'-bis(2-hydroxybenzyl)ethylenediamine-N,N'-diacetic acid, ethylenediamine-N,N'-diacetic acid, ethylenediamine-N,N'-dipropionic acid, triethylenetetraaminehexaacetic acid, ethylenediamine-N,N'-bis(methylenephosphonic acid), iminodiacetic acid, monosodium-N-lauryl-β-iminodipropionic acid (sodium lauriminodipropionate, Deriphat®160C), N,N-bis(2-hydroxyethyl)glycine, 1,3-diamino-2-hydroxypropanetetraacetic acid, 1,2-diaminopropanetetraacetic acid, ethylenediaminetetrakis(methylenephosphonic acid), N-(2-hydroxyethyl)iminodiacetic acid, biphosphonates, editronate, and salts thereof.

The debridement compositions can also contain chlorophyllin and its water-soluble derivatives in order to reduce local inflammation, promote healing, and control odor. It has been reported that in treating wounds that require debridement, some of the end products of proteolysis are mucoproteins, which often produce an irritating action and other deleterious actions on the tissue in contact with said end products. In order to control such undesirable effects, the incorporation of a water-soluble chlorophyll derivative has been incorporated into a proteolytic debridement formulation, generally in an amount of 0.05 to 1% by weight of the total composition, and preferably in an amount of 0.1% to 0.5% (U.S. Pat. No. 2,917,433). The water-soluble chlorophylls which may be used for the aforementioned purpose are exemplified by those disclosed in U.S. Pat. No. 2,120,667, including especially sodium or potassium copper chlorophyllin, sodium or potassium magnesium chlorophyllin and sodium or potassium iron chlorophyllin. The preferred water-soluble chlorophyll for this purpose was a mixture of sodium and potassium copper chlorophyllin, predominantly the potassium salt.

Other applications of chlorphyllin in wound treatment are exemplified by International Patent Publication Number WO 20081063229, wherein a protease enzyme debridement composition is a hydrophilic ointment that additionally comprises a supplemental agent that minimizes damage to healthy normal cells from compounds released by dying cells, wherein the agent is optionally sodium copper chlorophyllin, wherein the range of the stoichiometric ratio of moles of chlorophyllin administered to moles of debridement enzyme administered is optionally 0.1 to 10.0, 0.3 to 3.0, or 1.0.

Sodium copper chlorophyllin is also a food coloring agent and is known as natural green 3. Its addition to a debridement product also adds coloration, which is helpful in visualizing the removal of the debridement composition.

If pain reduction is required during debridement, the formulation can further comprise analgesic agents, anesthetic agents, and neuropathic pain agents, such as lidocaine, capsaicin, benzocaine, tetracaine, prilocaine, bupivacaine, levobupivacaine, procaine, carbocaine, etidocaine, mepivacaine, nortripylene, amitriptyline, pregabalin, diclofenac, fentanyl, gabapentin, non-steroidal anti-inflammatory agents, salicylates, combinations thereof, and the like.

Whereas $\alpha$-amylases catalyze the hydrolysis of internal $\alpha$-(1-4)-linkages of glucose polymers as their main reaction, some $\alpha$-amylases, particularly saccharifying amylases, however, catalyze transfer reactions in addition to hydrolysis (U.S. Pat. No. 8,486,664; International Patent Application Number WO 2012/013646). These $\alpha$-amylases are capable of transferring glycoside residues to low molecular weight alcohols as well as to water, a property related to the transferase activity of the glycosidases. It is not known whether such a transglycosylation process is operative in the debridement of necrotic tissue as related to this invention.

In some embodiments, a kit that includes a container containing debridement composition according to any of the variations described herein, and instructions for using the debridement composition for debridement of devitalized tissue is described. The instructions can include contacting the debridement composition with an area of skin in need of debridement. The instructions can include repeating the contacting step at regular intervals. The regular intervals can be at least once a day, or at least twice a day (every 12 hours), or at least three times a day (every 8 hours). The instructions can include mixing and or diluting the debridement composition in a solvent or other carrier liquid. The instructions can include removal of the necrotic tissue treated debridement composition by wiping and by solvent rinsing.

A method of debridement of devitalized tissue is also described. The method can include contacting a debridement composition according to any of the variations described herein with an area of skin in need of debridement, such as by a powder, liquid, gel, hydrogel, foam, paste, spray, or film. In some embodiments, the debridement composition is applied to a wound dressing, such as gauze, cloth, fiber, alginate, hydrocolloid, composite, or film. In some embodiments, the wound dressing is composed of natural or synthetic components, or combinations thereof. The method can also include abrading and/or removing the debridement composition after a given period of time. The method can include repeating the contacting step at regular intervals. In some embodiments, the regular intervals can be at least once a day, or at least twice a day (every 12 hours), or at least three times a day (every 8 hours). In some embodiments, the method also includes removing debrided tissue from the area of skin.

It is an object of the compositions, kits, and methods described herein to provide for enzymatic debridement of necrotic debris and eschar.

It is an object of the compositions, kits, and methods described herein to provide for enzymatic debridement treatment of chronic wounds, acute wounds and burn wounds.

It is a further object of the compositions, kits, and methods described herein to provide enzymatic debridement of necrotic tissue not based predominantly on peptide cleavage/hydrolysis by proteases.

It is a further object of the compositions, kits, and methods described herein to provide enzymes for debridement that cleave carbohydrate $\alpha$-1,4-glycodisic linkages in polysaccharides or glycosidic linkages with proteins.

It is a further object of the compositions, kits, and methods described herein to provide carbohydrate hydrolytic enzymes for enzymatic debridement based on the amylase family of enzymes.

It is a further object of the compositions, kits, and methods described herein to treat necrotic wounds comprising the step of administering an effective amount of an amylase enzyme.

It is a further object of the compositions, kits, and methods described herein to provide carbohydrate hydrolytic enzymes for enzymatic debridement based upon $\alpha$-amylase.

It is a further object of the compositions, kits, and methods described herein to provide carbohydrate hydrolytic enzymes for enzymatic debridement based upon $\beta$-amylase.

It is a further object of the compositions, kits, and methods described herein to provide carbohydrate hydrolytic enzymes for enzymatic debridement based upon $\gamma$-amylase in combination with $\alpha$-amylase and with $\beta$-amylase.

It is a further object of the compositions, kits, and methods described herein to provide carbohydrate hydrolytic enzymes for enzymatic debridement based upon the amylase family, selected from combinations of α-amylase, with β-amylase, and γ-amylase.

It is a further object of the compositions, kits, and methods described herein to provide for enzymatic tissue debridement based predominantly on α-amylase, with a minimum (20 wt % or less) of other families of enzymes.

It is a further object of the compositions, kits, and methods described herein to provide for enzymatic tissue debridement wherein families of hydrolytic cleavage enzymes other than amylases include 20 wt % or less of proteases, chondroitinases, hyaluronidases, lipases, glycosidases, heparanases, dermatanases, pullulanases, N-acetylglucosaminidase, lactases, phospholipases, transglycosylases, esterases, thioester hydrolyases, sulfatases, escharases, nucleases, phosphatases, phosphodiesterases, mannanases, mannosidases, isoamylases, lyases, inulinases, keratinases, tannases, pentosanases, glucanases, arabinosidases, pectinases, cellulases, chitinases, xylanases, cutinases, pectate lyases, hemicellulases, combinations thereof, and the like.

It is a further object of the compositions, kits, and methods described herein to provide for enzymatic tissue debridement wherein families of enzymes other than amylases include 20 wt % or less of oxidases, peroxidases, glucose oxidases, catalases, oxidoreductases, phenoloxidases, laccases, lipoxygenases, isomerases, ligninases, combinations thereof, and the like.

It is a further object of the compositions, kits, and methods described herein to provide for debridement based upon α-amylase, wherein the α-amylase is administered as a powder, gel, paste, liquid, ointment, foam, bandage, mesh or dressing.

It is a further object of the compositions, kits, and methods described herein to provide for debridement based upon α-amylase that is administered topically or subcutaneously.

It is a further object of the compositions, kits, and methods described herein to provide for debridement based upon α-amylase, wherein the α-amylase is applied in a hydrophilic or aqueous medium.

It is a further object of the compositions, kits, and methods described herein to provide a pleasing fragrance to the debridement compositions.

It is a further object of the compositions, kits, and methods described herein to apply chlorophyllin to a wound to reduce local inflammation, promote healing, and control odor.

It is a further object of the compositions, kits, and methods described herein to provide a wound dressing for amylase treatment comprised of gauze, mesh, cloth, fiber, foam or film.

It is a further object of the compositions, kits, and methods described herein to provide for preserved formulations of amylase.

It is a further object of the compositions, kits, and methods described herein to provide for antimicrobial formulations of amylase.

It is a further object of the compositions, kits, and methods described herein to provide for antimicrobial formulations of amylase that reduce or eliminate Gram positive and Gram negative bacteria in wounds and biological surfaces.

It is a further object of the compositions, kits, and methods described herein to provide for antimicrobial formulations of amylase that reduce or eliminate yeast in wounds and biological surfaces.

It is a further object of the compositions, kits, and methods described herein to provide for antimicrobial amylase formulations that incorporate antimicrobial essential oils to augment the antimicrobial activity of the compositions.

It is a further object of the compositions, kits, and methods described herein to provide for debridement based upon α-amylase by a surfactant capable of solubilizing, swelling, or hydrating devitalized tissue or eschar.

It is a further object of the compositions, kits, and methods described herein to provide for α-amylase-based debridement a hydrophilic polymer capable of increasing viscosity or causing gelation of the formulation.

It is a further object of the compositions, kits, and methods described herein to provide amylase in kit form for treatment of wounds and necrotic tissue.

EXAMPLES

The following ingredients and their abbreviations are used in this invention:

Enzymes

α-Amylase #1, porcine pancreas, 30 U/mg, Sigma Aldrich, A3176-500KU, lot SLBF3831V.

α-Amylase #2, porcine pancreas, (contains 0.2% protease), 230 U/mg, Lee BioSolutions, lot M60404.

α-Amylase #3, porcine pancreas, (contains 0.05% protease), 210 U/mg, Lee BioSolutions, lot P70442.

α-Amylase #4, human saliva, 117.5 U/mg, Sigma Aldrich, lot SLBB8953V.

α-Amylase #5, *Bacillus licheniformis*, 500-1500 U/mg. Sigma Aldrich, lot SLBG8595V.

α-Amylase #6, *Bacillus subtilis* spp., powder, 7278 U/mg. Dyadic International, lot ADY4001.

α-Amylase #7, *Bacillus subtilis* spp., solution, 1269 U/mg. Dyadic International, lot ASP3001.

β-Amylase, barley, 41.6 U/mg, Sigma Aldrich, lot SLBC2932V.

γ-Amylase #1, *Aspergillus niger*, 129.2 U/mg, Sigma Aldrich, lot BCBD1453V.

γ-Amylase #2, *Rhizopus* spp., MyBiosource Inc., lot 22200303.

Bromelain, pineapple stem, 3-7 U/mg, Sigma Aldrich, lot SLBG2202V

Collagenase, Type I, *Clostridium histolyticum*, 125 U/mg, Sigma Aldrich, C0130-100UG, lot SLBH5757V.

Lipase #1, porcine pancreas, 30-90 U/mg, Sigma Aldrich, lot SLBH6427V.

Lipase #2, porcine pancreas, (contains <0.05% protease), 360 U/mg, Lee BloSolutions, 400-10, lot R24160.

Other Ingredients

AC, Antimicrobial Composition, Water, 95.5 wt %, PHMB 0.1 wt %, EDTA 0.065 wt %, P407 2 wt %, HPMC, 2 wt %, SC50, 0.3 wt %, SC10, 0.1 wt %, pH 5.5.

CHG, Chlorhexidine gluconate, Spectrum Chemicals, lot ZQ1023.

Collagen, type I, rat tail, Corning Inc., 3542368, lot 3298599.

DC 193, PEG-12 Dimethicone, Dow Corning, lot 0002250697

Dulbecco's Phosphate Buffered Saline, DPBS, pH 7.1, Sigma Aldrich, D8537, lot RNBC1143.

EDTA, Ethylenediaminetetraacetic acid di-, tri-sodium salts, Spectrum Chemicals, lots 1AE0430, YL0044.

Glycerin, Quality Choice, lot 519675.

Hydroxypropylmethylcellulose (HPMC), Amerchol Corp., lot WF15012N01.

Mineral Oil, CVS, lot 5BF0201.

PEG 400, Poly(ethylene glycol), 400 $M_n$, Sigma-Aldrich, lot MKBD2642V.
Petrolatum, Vaseline, lot 02011HU00.
PHMB, Poly(hexamethylene biguanide hydrochloride), Cosmocil™ CQ, Arch Chemical, lot 11RC116995.
P407, Poloxamer 407, Pluronic F127, Spectrum Chemicals, lot 1AD0265.
Polymer JR-30M, Amerchol, lot XL2850GRXA.
SC10, Sensiva® SC 10, 1,2-Dihydroxyoctane), Schülke & Mayr, lot 1178933.
SC50, Sensiva® SC 50, Glycerol 1-(2-ethylhexyl) ether), Schülke & Mayr, lot 1179743.
Sodium Hydroxide, Puritan 50% NaOH, UN1824, lot 011043.
Urea, Sigma Aldrich, lot SLBF4607V.
Water, Deionized, adjusted to pH 7.

Collagen Gel Digestion

In order to determine if an α-amylase contained a protease and thus was able to cleave a collagen gel (i.e., a protein-based gel), collagen gel digestion was studied by rheology under varied frequency conditions using α-amylase and collagenase as potential digesting enzymes. If α-amylase had no digestion of the collagen gel, its debridement activity of tissue would not be based upon any contamination by a protease, and thus not by hydrolysis of peptide bonds of collagen polymer chains.

Collagen gels were prepared at 2.0 mg/mL using collagen type I. Gels were prepared by mixing 500 µL collagen (~4.1 mg/mL), 500 µL Dulbecco's phosphate buffered saline (DPBS), and 10 µL 1 N NaOH (diluted from Puritan 50% NaOH). Solid collagen hydrogels were formed after 30 min in a 37° C. incubator. Gels were incubated at 37° C. for 24 hours with the following enzymes:

2 mg (250 U) collagenase
8 mg (250 U) α-amylase #1

Rheological testing was conducted on an Anton Paar MCR 302 rheometer using a 25 mm parallel plate (for solid gels) and 25 mm cone and plate (for completely liquefied gels, i.e., collagen gel treated with collagenase). All frequency sweeps were conducted at 37° C. and 1% strain (linear viscoelastic region as determined by a strain amplitude sweep). The data are shown in FIG. 1, for the storage and loss moduli vs. frequency, and in FIG. 2, for the complex moduli for untreated collagen gel, for amylase treated collagen gel and collagenase treated collagen gel.

Figure 1:
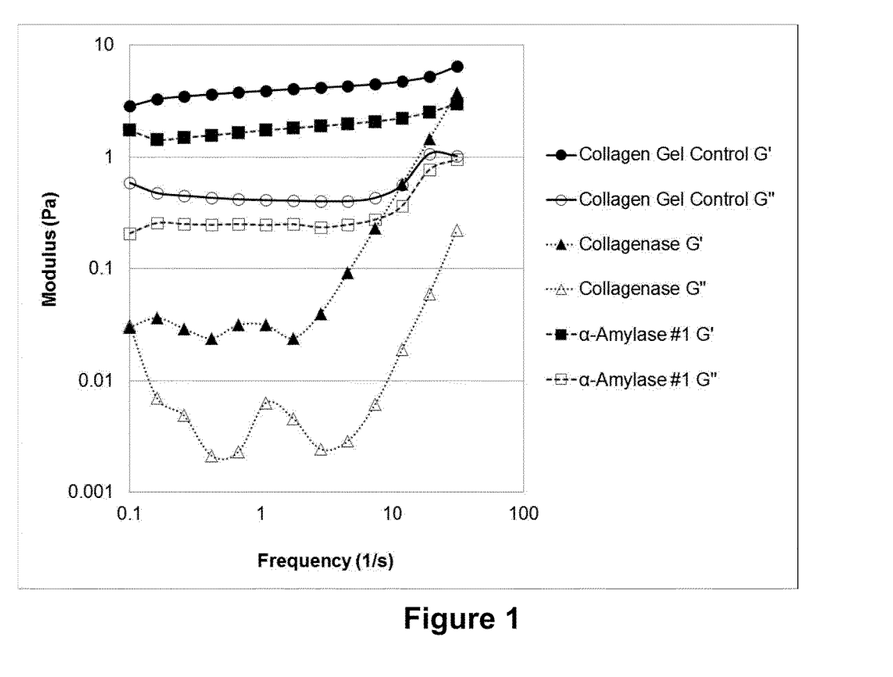
FIG. 1 is a graph of frequency versus modulus for collagen gels before and after treatment with different enzymes.

In FIG. 1, storage (G') and loss (G") moduli versus frequency are presented for untreated collagen gel controls, collagen gels treated with 250 Units collagenase, and collagen gels treated with 250 Units α-amylase #1. The storage modulus represents the solid-like nature and the loss modulus represents the liquid-like nature of the viscoelastic collagen gel. There is no significant difference between storage and loss moduli between the untreated collagen gel and the gel treated with α-amylase #1, demonstrating no collagen (protein) gel digestion by α-amylase. The protease collagenase completely liquefied the collagen gel, which is demonstrated by the significantly lower storage and loss moduli.

Figure 2:
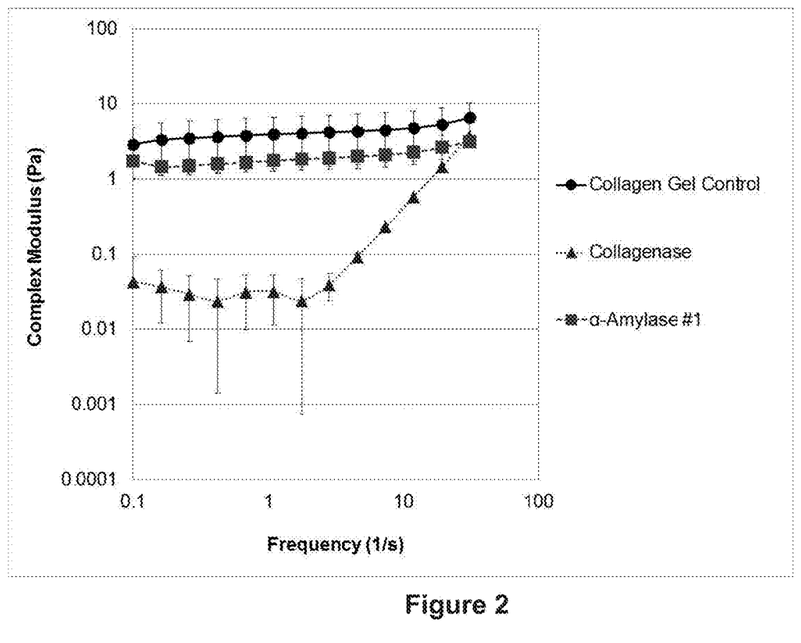
FIG. 2 is a graph of frequency versus complex modulus for collagen gels before and after treatment with different enzymes.

In FIG. 2, complex modulus (G*) is plotted versus frequency for untreated collagen gel controls, collagen gels treated with 250 Units collagenase, and collagen gels treated with 250 Units α-amylase #1. Complex modulus accounts for the storage modulus (solid-like behavior) and loss modulus (liquid-like behavior), which correlates with the gel's stiffness. α-Amylase #1 does not digest the collagen gels compared to the untreated collagen gel control (no statistically significant difference in complex moduli).

These Figures demonstrate that collagenase, a protease, completely liquefied the collagen gels within 24 hours, whereas α-amylase #1, a protein enzyme noted for cleavage of α-linked polysaccharides, such as those in starch and glycogen, did not digest the collagen gel compared to the untreated collagen gel control (no statistically significant difference in storage moduli, loss moduli, or complex moduli). From these Figures, moduli are observed to increase with frequency due to the viscoelastic nature of the polymer (collagen) tested. At high frequencies, the collagen polymer chains do not have time to relax, resulting in an observed stiffer viscoelastic behavior. The data for collagen gel treated with collagenase appears noisy due to the liquid-like nature of the resulting digestion of the collagen gel. Collagenase completely degraded and liquefied the collagen gel, and the resulting enzymatically degraded solution had to be evaluated using cone and plate geometry on the rheometer. While the gel was completed liquefied, the resulting solution was still viscoelastic due to the nature of the collagen and peptides remaining in the solution.

The rheology data supports the debridement activity on devitalized tissue by α-amylase as not being dependent on contamination by a protease.

Method for Evaluating Digestion Efficacy of Various Enzymes ex vivo

In U.S. Pat. No. 8,119,124, an in vivo (ex vivo) burn wound model was reported using the skin of young swine because of its similarity to that of humans. In our investigation, several samples of frozen pig skin were obtained from Culebra Meat Market, San Antonio, Tex., and used as a debridement analog. For each digestion experiment, the pig skin was boiled in water for 1 minute, and then cut into small square pieces. The boiled pig skin was weighed immediately prior to the application of a debridement formulation. It was then incubated with 1 gram of each debridement formulation for 16 hours at 34° C. in water at pH 7, and wiped gently with a piece of paper towel to remove any digested tissue. The remaining tissue was then weighed. As a control, boiled pig skin was treated without active enzyme by the same procedure. The percent digestion of pig skin was calculated using the following formulation:

$$\% \text{ digested pig skin} = \frac{W_2 \text{ enz}}{W_1 \text{ enz} \cdot \frac{W_2 \text{ veh}}{W_1 \text{ veh}}} * 100\%$$

where
$W_1$ enz: weight of pig skin prior to digestion in a formulation that contains one or more active enzymes.
$W_1$ veh: weight of pig skin prior to digestion in the same formulation except without any active enzymes.
$W_2$ enz: weight of pig skin after digestion in a formulation that contains one or more active enzymes.
$W_2$ veh: weight of pig skin after digestion in the same formulation except without any active enzymes.

Digestion Results, Pig Skin

Amylase from different sources, or at different activity levels expressed in Units (U), showed different levels of ex vivo debridement activity (Table 1). α-Amylase from porcine pancreas from both Sigma Aldrich (α-amylase #1) and Lee BioSolutions (α-amylase #2, α-amylase #3) showed high debridement efficacy, where 1 gram of formulation contains 250 U of enzyme. Surprisingly, the α-amylase (Lee BioSolutions, 0.2% protease) that contained a higher amount of protease impurity (α-amylase #2) had a slightly lower debridement efficacy than the α-amylase that contained a lower amount of protease impurity (Lee BioSolutions, 0.05% protease) (α-amylase #3), further supporting the conclusion that amylase debridement activity is not a result of protease contamination. α-Amylase from human saliva (α-amylase #4) was ineffective in digesting pig skin at the concentration studied. The activity of α-amylase derived from bacteria is highly variable depending on the bacterial strain and the vendor. The α-amylase from *Bacillus licheniformis* (α-amylase #5) showed very weak debridement efficacy, whereas the α-amylase from *Bacillus subtilis* spp. showed high debridement efficacy (α-amylase #6, α-amylase #7), particularly at an activity of 250,000 Units of enzyme in 1 gram of formulation. β-Amylase showed some activity in digesting pig skin based upon its ability to act upon the same substrates as α-amylase but with a different catalytic mechanism, whereas γ-amylase #1 and #2 were ineffective in this debridement model.

TABLE 1

Ex vivo debridement efficacy of amylases from various sources on boiled pig skin in water

| formulation | formulation ratio (wt %) | formulation (Units) | % digested |
|---|---|---|---|
| H$_2$O/α-amylase #1 | 99.2/0.8 | 1 g/250U | 96.30% |
| H$_2$O/α-amylase #2 | 99.891/0.109 | 1 g/250U | 96.60% |
| H$_2$O/α-amylase #3 | 99.88/0.12 | 1 g/250U | 97.90% |
| H$_2$O/α-amylase #4 | 99.8/0.2 | 1 g/250U | 4.30% |
| H$_2$O/α-amylase #5 | 99.95 g/0.05 | 1 g/250U | 0% |
| H$_2$O/α-amylase #5 | 99.9/0.1 | 1 g/500U | 13.50% |
| H$_2$O/α-amylase #6 | 99.9966/0.0033 | 1 g/250U | 17.50% |
| H$_2$O/α-amylase #6 | 99.966/0.034 | 1 g/2,500U | 70.80% |
| H$_2$O/α-amylase #6 | 96.6/3.4 | 1 g/250,000U | 100% |
| H$_2$O/α-amylase #7 | 99.9803/0.0197 | 1 g/250U | 15.00% |
| H$_2$O/α-amylase #7 | 99.803/0.197 | 1 g/2,500U | 77.60% |
| H$_2$O/α-amylase #7 | 80.3/19.7 | 1 g/250,000U | 100% |
| H$_2$O/β-amylase | 99.4/0.6 | 1 g/250U | 18.60% |
| H$_2$O/β-amylase | 94/6 | 1 g/2500U | 38.90% |
| H$_2$O/γ-amylase #1 | 99.8/0.2 | 1 g/250U | 0% |
| H$_2$O/γ-amylase #1 | 99/1 | 1 g/1,250U | 0% |
| H$_2$O/γ-amylase #1 | 98/2 | 1 g/2,500U | 0% |
| H$_2$O/γ-amylase #2 | 99.4/0.6 | 1 g/250U | 0% |

In Table 2 are listed the effects of various additives and excipients on the debridement efficacy of α-amylase #1 with boiled pig skin. Included is a DPBS buffered solution, a formulation in mineral oil, a formulation of a hydrophilic, a viscosity increasing polymer, HPMC, in DPBS, and a formulation with a viscosity increasing cationic polymer, Polymer JR (cationic hydroxyethylcellulose). The results are compared to α-amylase #1 in water at pH 7. Each formulation contained the same amount of α-amylase #1, namely 250 Units. It is seen that the formulation consistency affected the amylase debridement efficacy. The addition of DPBS buffer appeared to enhance the debridement efficacy compared to α-amylase in water, whereas mineral oil greatly decreased the debridement efficacy, presumably because of the lack of water for enzymatic solubility and activity; the added water-soluble polymers of neutral cellulose-based HPMC in DPBS and cationic cellulose-based Polymer JR in water somewhat decreased the debridement efficacy, possibly because of a lower content of water in their formulations compared to α-amylase #1 by itself in water.

TABLE 2

Ex vivo debridement efficacy of α-amylase #1 in various formulations on boiled pig skin

| formulation | formulation ratio (wt %) | formulation (Units) | % digested |
|---|---|---|---|
| H$_2$O/α-amylase #1 | 99.2/0.8 | 1 g/250U | 96.30% |
| DPBS/α-amylase #1 | 99.2/0.8 | 1 g/250U | 100% |
| Mineral oil/α-amylase #1 | 99.2/0.8 | 1 g/250U | 62.90% |
| HPMC/DPBS/α-amylase #1 | 5/94.2 g/0.8 | 0.05 g/0.95 g/250U | 80.10% |
| Polymer JR-30M/H$_2$O/α-amylase #1 | 5/94.2 g/0.8 | 0.05 g/0.95 g/250U | 84.30% |

In Table 3 are described combinations of α-amylase and IS-amylase using bacterial α-amylase from *Bacillus subtilis* (α-amylase #6) in conjunction with plant derived β-amylase. In this model, the greater amount of β-amylase appeared to hinder the overall digestion of the boiled pig skin.

TABLE 3

Ex vivo debridement efficacy of boiled pig skin by α-amylase #6 with β-amylase in water

| formulation | formulation ratio (wt %) | formulation (Units) | % digested |
|---|---|---|---|
| H$_2$O/α-amylase #6 | 99.66/0.34 | 1 g/250U | 79.20% |
| H$_2$O/α-amylase #6/β-amylase | 96.6/0.34/3.16 | 1 g/250U/131U | 53.70% |
| H$_2$O/α-amylase #6/β-amylase | 99.32/0.34/0.34 | 1 g/250U/14U | 72.30% |

In Table 4, the addition of another non-proteolytic hydrolytic enzyme, lipase, to α-amylase #3 on the digestion of boiled pig skin is given, using amylase contents of 100 wt %, 90 wt %, and 80 wt % to lipase. Lipase is noted for its ability to catalyze the hydrolysis of ester bonds in lipids (triglycerides, fats, and oils). There are multiple sources of lipase as it is produced by the pancreas, liver, intestine, tongue, stomach, and many other cells, as well as the seeds of plants. The addition of lipase to α-amylase could be a major adjunct in debridement wherein fatty tissue is involved. In the pig model studied, the % boiled pig skin digested was relatively constant for the three samples studied, using a total enzyme concentration of 0.2 wt %, even though the amount of amylase #3 decreased with increasing lipase content, indicating that both non-proteolytic enzymes contributed to the digestion of boiled pig skin.

TABLE 4

Ex vivo debridement efficacy of boiled pig skin by α-amylase #3 with lipase #2 in water

| formulation | formulation ratio (wt %) | formulation (Units) | % digested |
|---|---|---|---|
| H$_2$O/α-amylase #3 | 99.8/0.2 | 1 g/420U | 83.90% |
| H$_2$O/α-amylase #3/lipase #2 | 99.8/0.18/0.02 | 1 g/378U/72U | 84.10% |
| H$_2$O/α-amylase #3/lipase #2 | 99.8/0.16/0.04 | 1 g/336U/144U | 81.20% |

In Table 5 are given the results of pig skin digested by α-amylase #1 in water with the keratolytic agent urea, with chlorophyllin for reducing local inflammation, promoting healing, and controlling odor, and with a combination of urea and chlorophyllin. All solutions with chlorophyllin were green colored. It is seen that a different source of pig skin, compared to that of Table 1, done under similar conditions, had a reduced digestion level. The addition of urea appeared to increase the digestion efficacy by α-amylase, while the addition of two concentrations of chlorophyllin appeared to decrease the amylase efficacy. A combination of the three ingredients gave a digestion efficacy greater than chlorophyllin and α-amylase, and less than that of urea and amylase, or α-amylase by itself.

TABLE 5

Ex vivo debridement efficacy of boiled pig skin by α-amylase #1 with urea and chlorophyllin in water

| formulation | formulation ratio (wt %) | formulation (Units) | % digested |
|---|---|---|---|
| $H_2O$/α-amylase #1 | 99.2/0.8 | 1 g/250U | 78.60% |
| $H_2O$/urea/α-amylase #1 | 89.2/10/0.8 | 1 g/250U | 84.90% |
| $H_2O$/chlorophyllin/α-amylase #1 | 98.7/0.5/0.8 | 1 g/250U | 54.80% |
| $H_2O$/chlorophyllin/α-amylase #1 | 98.2/1/0.8 | 1 g/250U | 59.30% |
| $H_2O$/urea/chlorophyllin/α-amylase #1 | 88.7/10/0.5/0.8 | 1 g/250U | 67.20% |

Necrotic tissue is susceptible to bacterial infection, which further impedes wound healing, and may induce sepsis in severe cases. Because of the possibly of infection in necrotic wounds and damaged and irritated tissue, addition of a biological agent that hinders or eradicates microorganisms is desired. In this regard, we investigated two antimicrobial biguanides used in wound care, poly(hexamethylene biguanide hydrochloride) (PHMB) and chlorhexidine digluconate (CHG). Table 6 is a comparison of three formulations of aqueous solutions of PHMB with α-amylase #6 and CHG with α-amylase #6, all at the same wt % of α-amylase #6. For the PHMB-based solutions, these activities were analogous or slightly greater than that of α-amylase by itself, although the higher PHMB level of 0.15 wt % (1500 ppm) may have slightly decreased the amylase activity. The use of CHG, however, appeared to decrease markedly the amylase digestion ability.

TABLE 6

Ex vivo debridement of pig skin by α-amylase #6 with PHMB and CHG in water

| formulation | formulation ratio (wt %) | formulation (Units) | % digested |
|---|---|---|---|
| $H_2O$/α-amylase #6 | 99.66/0.34 | 1 g/25,000U | 83.90% |
| $H_2O$/PHMB/α-amylase #6 | 99.51/0.15/0.34 | 1 g/25,000U | 81.30% |
| $H_2O$/PHMB/α-amylase #6 | 99.56/0.1/0.34 | 1 g/25,000U | 84.90% |
| $H_2O$/PHMB/α-amylase #6 | 99.61/0.05/0.34 | 1 g/25,000U | 86.80% |
| $H_2O$/CHG/α-amylase #6 | 97.66/2/0.34 | 1 g/25,000U | 60.50% |

Digestion Results, Rat Skin

Freshly excised rat skin tissue was obtained from two adult rats 9 and 11 months of age from the Laboratory Animal Resources Center at the University of Texas at San Antonio, San Antonio, Tex., under an IACUC approved protocol. A large piece of skin was retrieved from the back of each male Sprague-Dawley rat. Half of the skin was cut and boiled in water for 60 seconds. Both the boiled and unboiled halves of the skin were cut into smaller pieces and trimmed so that each small piece weighed from 0.23 g to 0.25 g. One small piece of skin was soaked in 1 gram of each debridement formulation and incubated at 34° C. to debride for 24 hours. After the 24-hour incubation, the skin was removed from the debridement formulation. The debrided skin (soft and mushy tissue) was gently wiped with paper towels, and the remaining non-debrided skin was weighed. The percent of debrided skin was then calculated based on the weight before and after the debridement procedure.

Tables 7 and 8 present the debridement results of freshly excised rat skin from that which was debrided under unboiled and boiled conditions, respectively, using the amylolytic enzymes α-amylase #1 and α-amylase #6 as well as the protease enzymes of bromelain and collagenase, all in water at pH 7. For the unboiled rat skin (Table 7), it is seen that the two protease enzymes were more effective than either amylase, with collagenase being the most effective in digestion of rat skin at 79%. However, for boiled rat skin (Table 8), which is more analogous to devitalized, necrotic tissue, the amylolytic enzymes were comparable to the proteolytic enzymes in their ability to digest rat skin.

TABLE 7

Ex vivo debridement of unboiled rat skin by α-amylase, bromelain, and collagenase in water

| formulation | formulation ratio (wt %) | formulation (Units) | % digested |
|---|---|---|---|
| $H_2O$/α-amylase #1 | 99.2/0.8 | 1 g/250U | 31.80% |
| $H_2O$/α-amylase #6 | 99.66/0.34 | 1 g/25,000U | 29.80% |
| $H_2O$/bromelain | 90/10 | 1 g/250U | 51.90% |
| $H_2O$/collagenase | 99.8/0.2 | 1 g/250U | 79% |

TABLE 8

Ex vivo debridement of boiled rat skin by α-amylase, bromelain, and collagenase in water

| formulation | formulation ratio (wt %) | formulation (Units) | % digested |
|---|---|---|---|
| $H_2O$/α-amylase #1 | 99.2/0.8 | 1 g/250U | 86.80% |
| $H_2O$/α-amylase #6 | 99.66/0.34 | 1 g/25,000U | 90.40% |
| $H_2O$/bromelain | 90/10 | 1 g/250U | 92.90% |
| $H_2O$/collagenase | 99.8/0.2 | 1 g/250U | 86% |

If necrotic tissue is infected with a microbial biofilm, potentially further covering the necrotic tissue with additional polysaccharides (a component of an extracellular polymeric substance, sometimes referred to as slime) emanating from the biofilm microorganisms, which may be potentially bacterial in origin, removal or reduction of the biofilm may expedite the removal of necrotic or devitalized tissue. Tables 9 and 10 give the results of using an aqueous antimicrobial composition (AC) at pH 5.5 that has demonstrated efficacy in biofilm reduction (U.S. Pat. No. 8,829, 053). The antimicrobial composition contains a polymeric biguanide antimicrobial agent of PHMB, EDTA as a chelating and pH stabilizing agent, HPMC as a viscosity increasing polymer, a neutral surfactant of P407 for cleansing, and a combination of 2-ethylhexyl glycerin and 1,2-octanediol for emollient and antimicrobial properties. With the rat skin in an unboiled condition in the antimicrobial composition (Table 9), neither α-amylase #1 nor α-amylase #6 was as effective in digestion relative to that displayed by the same enzymes for unboiled rat skin in water (Table 7). Although bromelain in the antimicrobial composition was more effective than either amylase with the unboiled rat skin (Table 9), its digestion effect is less than that demonstrated for the digestion of the rat skin in water (Table 7). While collagenase was very effective for both unboiled and boiled rat skin digestion in water (Tables 7 and 8), for the unboiled rat skin in the presence of the aqueous antimicrobial composition, its effect in digestion was negligible (Table 9). This effect also occurred for collagenase with the boiled rat skin in the antimicrobial composition (Table 10), while α-amylase #1, α-amylase #6, and bromelain were highly effective (Table 10). Since the antimicrobial composition contains the metal ion chelating agent EDTA, this may have inactivated collagenase, which is a metalloproteinase (zinc endopeptidase). The calcium complex of amylase appears not to be affected by EDTA chelation, and the antimicrobial compositions of α-amylase would be an effective non-proteolytic treatment of necrotic tissue infected with microbial biofilm. The low debridement efficacy of α-amylase #1 and α-amylase #6 on unboiled, freshly excised rat skin in the antimicrobial composition (Table 9) also supports the amylolytic debridement composition being highly specific to devitalized tissue and not toward the surrounding living tissue.

TABLE 9

Ex vivo debridement of unboiled rat skin by α-amylase, bromelain, and collagenase in an antimicrobial composition

| formulation | formulation ratio (wt %) | formulation (Units) | % digested |
|---|---|---|---|
| AC/α-amylase #1 | 99.2/0.8 | 1 g/250U | 6.00% |
| AC/α-amylase #6 | 99.66/0.34 | 1 g/250U | 0% |
| AC/Bromelain | 90/10 | 1 g/250U | 18.20% |
| AC/collagenase | 99.8/0.2 | 1 g/250U | 4.70% |

TABLE 10

Ex vivo debridement of boiled rat skin by α-amylase, bromelain, and collagenase in an antimicrobial composition

| formulation | formulation ratio (wt %) | formulation (Units) | % digested |
|---|---|---|---|
| AC/α-amylase #1 | 99.2/0.8 | 1 g/250U | 96.50% |
| AC/α-amylase #6 | 99.66/0.34 | 1 g/250U | 100% |
| AC/bromelain | 90/10 | 1 g/250U | 100% |
| AC/collagenase | 99.8/0.2 | 1 g/250U | 0% |

Excipients

In addition to water and buffered solutions (Table 2), as well as being utilized in powder form, the amylases can be mixed with several excipients, including hydrophobic hydrocarbons of petrolatum and mineral oil, hydrophilic —OH containing alcohols of glycerin and PEG 400, and the amphiphilic liquid PEG-12 Dimethicone, a silicone polyether. In each case, α-amylase #1 could be dispersed in the excipient (Table 11). Other excipients could include various water-based buffers ranging in pH from 5.0-7.5, surfactants, silicones, polyether copolymers, polyoxyethylene ethers, vegetable and plant fats and oils, essential oils, hydrophilic and hydrophobic alcohols, vitamins, monoglycerides, laurate esters, myristate esters, palmitate esters, and stearate esters, preferably in liquid, gel, or paste form, combinations thereof, and the like. In some embodiments, excipients can be present in an amount ranging from 0% to 99.9 wt % based on the weight of the debridement composition.

TABLE 11

Excipients for α-amylase #1

| formulation | formulation ratio (wt %) | formulation (Units) |
|---|---|---|
| petrolatum/α-amylase #1 | 99.2/0.8 | 1 g/250U |
| mineral oil/α-amylase #1 | 99.2/0.8 | 1 g/250U |
| glycerin/α-amylase #1 | 99.2/0.8 | 1 g/250U |

TABLE 11-continued

Excipients for α-amylase #1

| formulation | formulation ratio (wt %) | formulation (Units) |
|---|---|---|
| PEG 400/α-amylase #1 | 99.2/0.8 | 1 g/250U |
| DC 193/α-amylase #1 | 99.2/0.8 | 1 g/250U |

Effective α-Amylase Concentration

Figure 3:
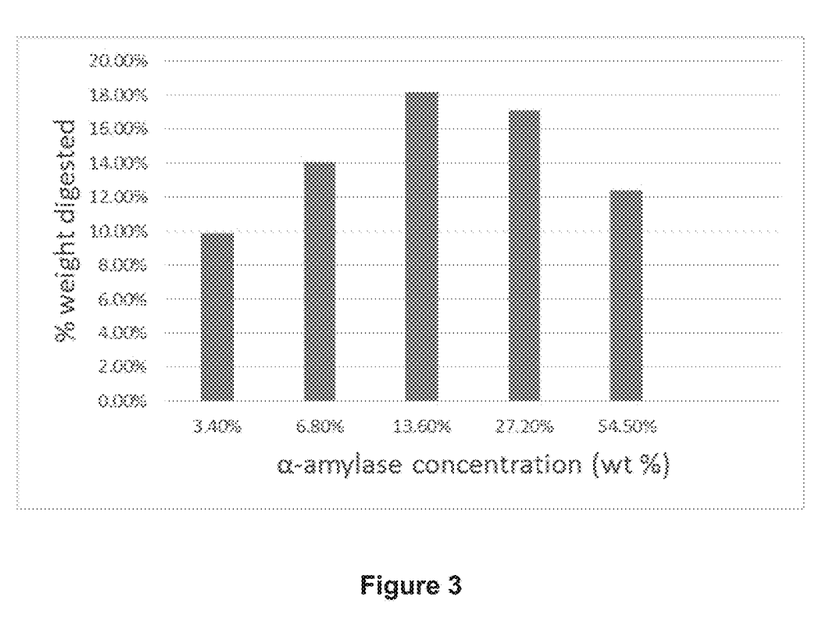
FIG. 3 is a graph of weight percent boiled pig skin digested verses α-amylase concentration after one hour at room temperature.

To determine the amount of α-amylase needed for debridement of necrotic tissue, a study was conducted to measure debridement efficacy (e.g., wt. % digested) verses α-amylase concentration. The results in FIG. 3 shows the concentration of α-amylase #6 versus the percent by weight of boiled pig skin digested in one hour at room temperature. The bell-shaped curve shows that debridement activity occurs at a maximum amylase concentration in the range of between 13.6 to 27.2 wt %, though the efficacy is 10 wt % or greater over the entire range from 3.4% to 54.5% α-amylase.

While the above specification contains many specifics, these should not be construed as limitations on the scope of the invention, but rather as examples of preferred embodiments thereof. Many other variations are possible. Accordingly, the scope of the invention should be determined not by the embodiments illustrated, but by the appended claims and their legal equivalents.

The invention claimed is:

1. A tissue debridement composition comprising:
0.1 to 99.5 wt % of an amylase component and optionally a proteolytic enzyme component, wherein a ratio of the amylase component to the proteolytic enzyme component is at least 10:1 by weight; and
at least one pharmaceutically or cosmetically acceptable carrier or excipient in an amount of up to 99.9 wt %, wherein the percentages are based on a total weight of the debridement composition,
wherein said amylase component comprises at least 80% by weight of α-amylase from a source selected from a group consisting of porcine pancreas and Bacillus subtilis, and wherein the debridement composition is able to debride devitalized or necrotic tissue.

2. The composition according to claim 1, wherein said amylase component comprises up to 20% by weight of an amylase selected from a group consisting of β-amylase, γ-amylase, and combinations thereof.

3. The composition according to claim 1, further comprising up to 20% by weight of hydrolytic enzymes selected from a group consisting of proteases, chondroitinases, hyaluronidases, lipases, glycosidases, heparanases, dermatanases, pullulanases, N-acetylglucosaminidase, lactases, phospholipases, transglycosylases, esterases, thioester hydrolyases, sulfatases, escharases, nucleases, phosphatases, phosphodiesterases, mannanases, mannosidases, isoamylases, lyases, inulinases, keratinases, tannases, pentosanases, glucanases, arabinosidases, pectinases, cellulases, chitinases, xylanases, cutinases, pectate lyases, hemicellulases, and combinations thereof, wherein the percentage is based on the total weight of the amylase component and the hydrolytic enzymes.

4. The composition according to claim 1, further comprising up to 20% by weight of other enzymes selected from a group consisting of oxidases, peroxidases, glucose oxidases, catalases, oxidoreductases, phenoloxidases, laccases, lipoxygenases, isomerases, and ligninases, wherein the percentage is based on the total weight of the amylase component and the other enzymes.

5. The composition according to claim 1, further comprising at least one polymeric biguanide in an amount ranging from 0.01 weight percent to 1.0 weight percent based on the weight of the debridement composition.

6. The composition according to claim 5, wherein said polymeric biguanide comprises poly(hexamethylene biguanide) and its salts.

7. The composition according to claim 1, further comprising a water-soluble polymer at a concentration from 0.01 weight % to 50 weight % based on the weight of the debridement composition.

8. The composition according to claim 1, further comprising a chelating agent at a concentration from 0.01 weight % to 1 weight % based on a weight of the debridement composition.

9. The composition according to claim 1, further comprising a monoalkyl glycol selected from a group consisting of 1,2-propanediol (propylene glycol), 1,2-butanediol, 1,2-pentanediol, 1,2-hexanediol, 1,2-heptanediol, 1,2-octanediol (caprylyl glycol), 1,2-nonanediol, 1,2-decanediol, 1,2-undecanediol, 1,2-dodecanediol, 1,2-tridecanediol, 1,2-tetradecanediol, 1,2-pentadecanediol, 1,2-hexadecanediol, 1,2-heptadecanediol, 1,2-octadecanediol, 2-methyl-2,4-pentanediol, 1,3-butanediol, diethylene glycol, triethylene glycol, glycol bis(hydroxyethyl) ether, and combinations thereof.

10. The composition according to claim 1, further comprising a glycerol alkyl ether selected from a group consisting of 1-O-heptylglycerol, 1-O-octylglycerol, 1-O-nonylglycerol, 1-O-decylglycerol, 1-O-undecylglycerol, 1-O-dodecylglycerol, 1-O-tridecylglycerol, 1-O-tetradecylglycerol, 1-O-pentadecylglycerol, 1-O-hexadecylglycerol (chimyl alcohol), 1-O-heptadecylglycerol, 1-O-octadecylglycerol (batyl alcohol), 1-O-octadec-9-enyl glycerol (selachyl alcohol), glycerol 1-(2-ethylhexyl) ether, 2-ethylhexyl glycerin, glycerol 1-heptyl ether, glycerol 1-octyl ether, glycerol 1-decyl ether, and glycerol 1-dodecyl ether, glycerol 1-tridecyl ether, glycerol 1-tetradecyl ether, glycerol 1-pentadecyl ether, glycerol 1-hexadecyl ether, glycerol 1-octadecyl ether, and combinations thereof.

11. The composition according to claim 1, further comprising
at least one polymeric biguanide in an amount ranging from 0.01 weight % to 1.0 weight % based on the weight of the debridement composition,
a vicinal diol component selected from a group consisting of a monoalkyl glycol and a monoalkyl glycerol at a concentration of 0.05 weight % to 4 weight %, based on a weight of the debridement composition.

12. The composition according to claim 1, further comprising at least one analgesic agent, anesthetic agent, neuropathic pain agent, or a combination thereof.

13. The composition according to claim 12, wherein the at least one analgesic agent, anesthetic agent, or neuropathic pain agent is selected from a group consisting of lidocaine, capsaicin, benzocaine, tetracaine, prilocaine, bupivacaine, levobupivacaine, procaine, carbocaine, etidocaine, mepivacaine, nortripylene, amitriptyline, pregabalin, diclofenac, fentanyl, gabapentin, non-steroidal anti-inflammatory agents, salicylates, and combinations thereof.

14. The composition according to claim 1, wherein the debridement composition has a form selected from a group consisting of a powder, aqueous solution, organic liquid solution, silicone, gel, cream, film, latex, aerosol, slurry, paste, ointment and foam.

15. The composition according to claim 1, wherein said debridement composition is adsorbed on or in a dressing or a natural or synthetic fiber, mesh, hydrocolloid, alginate, hydrogel, semipermeable film, permeable film, or a natural or synthetic polymer.

16. The composition according to claim 1, further comprising a buffering agent.

17. A kit comprising:
a tissue debridement composition according to claim 1; and
instructions for debridement of devitalized tissue.

18. The kit according to claim 17, wherein said instructions comprise contacting the tissue debridement composition with an area of skin in need of debridement.

19. A method of debridement of devitalized tissue comprising contacting a tissue debridement composition according to claim 1 with an area of skin in need of debridement.

20. The method of claim 19, wherein said contacting step is repeated at least once a day.

21. The method of claim 19, further comprising removing debrided tissue from said area of skin.

22. The composition according to claim 1, wherein the amylase component is present in an amount ranging from 2 to 99.5 wt-% based on the total weight of the debridement composition.

* * * * *